United States Patent
Terada et al.

(10) Patent No.: US 10,226,198 B2
(45) Date of Patent: Mar. 12, 2019

(54) ELECTRODE ATTACHMENT STATE DETERMINATION SYSTEM, ELECTRODE ATTACHMENT STATE DETERMINATION METHOD, AND PROGRAM THEREOF

(75) Inventors: Yoshihisa Terada, Tokyo (JP); Koji Morikawa, Kyoto (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 1656 days.

(21) Appl. No.: 13/224,452

(22) Filed: Sep. 2, 2011

(65) Prior Publication Data

US 2012/0029336 A1  Feb. 2, 2012

Related U.S. Application Data

(63) Continuation of application No. PCT/JP2010/006828, filed on Nov. 22, 2010.

(30) Foreign Application Priority Data

Dec. 15, 2009  (JP) .................. 2009-283678

(51) Int. Cl.
  *A61B 5/0478* (2006.01)
  *A61B 5/048* (2006.01)
  (Continued)

(52) U.S. Cl.
  CPC .......... *A61B 5/048* (2013.01); *A61B 5/04004* (2013.01); *A61B 5/0478* (2013.01);
  (Continued)

(58) Field of Classification Search
  CPC ... A61B 5/0476; A61B 5/04012; A61B 5/048; A61B 5/0478; A61B 5/0006;
  (Continued)

(56) References Cited

U.S. PATENT DOCUMENTS

| | | | | |
|---|---|---|---|---|
| 4,579,125 A | * | 4/1986 | Strobl et al. | .................. 600/544 |
| 4,800,895 A | * | 1/1989 | Moberg | ................. A61B 5/048 |
| | | | | 600/544 |

(Continued)

FOREIGN PATENT DOCUMENTS

| | | |
|---|---|---|
| JP | 7-003347 U | 1/1995 |
| JP | 07-108848 A | 4/1995 |

(Continued)

OTHER PUBLICATIONS

Donchin et al., "The Mental Prosthesis: Assessing the Speed of a P300-Based Brain-Computer Interface", IEEE Transactions on Rehabilitation Engineering, vol. 8, No. 2, Jun. 2000, pp. 174-179.

(Continued)

*Primary Examiner* — Patricia Mallari
*Assistant Examiner* — Michael Catina
(74) *Attorney, Agent, or Firm* — Renner, Otto, Boisselle & Sklar, LLP

(57) ABSTRACT

An electrode attachment state determination system includes: an electroencephalogram measurement section for measuring an electroencephalogram signal of a user by using at least one set of electrodes including a ground electrode, a reference electrode, and a measurement electrode; a frequency analysis section for performing a frequency analysis of the electroencephalogram signal; an insufficient electrode determination section for extracting at least one parameter of a total frequency power and a noise amount from a result of the frequency analysis, and through a comparison of a value of the parameter against a predetermined threshold value, determining whether the ground electrode, the reference electrode, or the measurement electrode has an insufficient state of attachment; and an output section for, when an insufficient state of attachment is determined, presenting information indicating the insufficient state of electrode attachment to the user.

14 Claims, 25 Drawing Sheets

(51) Int. Cl.
*A61B 5/04* (2006.01)
*A61B 5/00* (2006.01)

(52) U.S. Cl.
CPC .......... *A61B 5/6843* (2013.01); *A61B 5/6803* (2013.01); *A61B 2560/0276* (2013.01); *A61B 2562/0215* (2017.08)

(58) Field of Classification Search
CPC ... A61B 5/6803; A61B 5/0484; A61B 5/6843; A61B 5/04004
See application file for complete search history.

(56) References Cited

U.S. PATENT DOCUMENTS

| | | | |
|---|---|---|---|
| 5,119,816 A | | 6/1992 | Gevins |
| 5,495,853 A | * | 3/1996 | Yasushi .......................... 600/545 |
| 6,067,467 A | * | 5/2000 | John .............................. 600/544 |
| 8,538,512 B1 | * | 9/2013 | Bibian ................. A61B 5/7235 600/544 |
| 2006/0241562 A1 | * | 10/2006 | John et al. ..................... 604/503 |
| 2009/0247835 A1 | * | 10/2009 | Voipio .......................... 600/301 |
| 2009/0247895 A1 | * | 10/2009 | Morikawa et al. ........... 600/544 |
| 2009/0259137 A1 | * | 10/2009 | Delic et al. .................... 600/545 |
| 2010/0191140 A1 | * | 7/2010 | Terada et al. ................. 600/544 |

FOREIGN PATENT DOCUMENTS

| | | |
|---|---|---|
| JP | 2006-006665 A | 1/2006 |
| JP | 2006-014833 A | 1/2006 |
| JP | 2006-212348 A | 8/2006 |

OTHER PUBLICATIONS

Chinese Search Report for corresponding Chinese Patent Application No. 201080023316.2 dated Dec. 4, 2013 with English translation.

* cited by examiner

[UNIT : $\mu V\wedge2$]

| | NORMAL | SHIFTING MEASUREMENT ELECTRODE 1 | SHIFTING MEASUREMENT ELECTRODE 2 | SHIFTING REFERENCE ELECTRODE | DISENGAGING GROUND |
|---|---|---|---|---|---|
| Ch1 AMOUNT OF MIXED AC NOISE | 82.3 | 80.3 | 81.4 | 42.9 | 35502.3 |
| Ch2 AMOUNT OF MIXED AC NOISE | 121.8 | 123.1 | 124.8 | 56.1 | 151739.9 |
| Ch1 TOTAL FREQUENCY POWER | 5.2 | 93.7 | 4.6 | 357.6 | 594.1 |
| Ch2 TOTAL FREQUENCY POWER | 2.8 | 3.4 | 67.1 | 194.6 | 2430.6 |

502  503  501

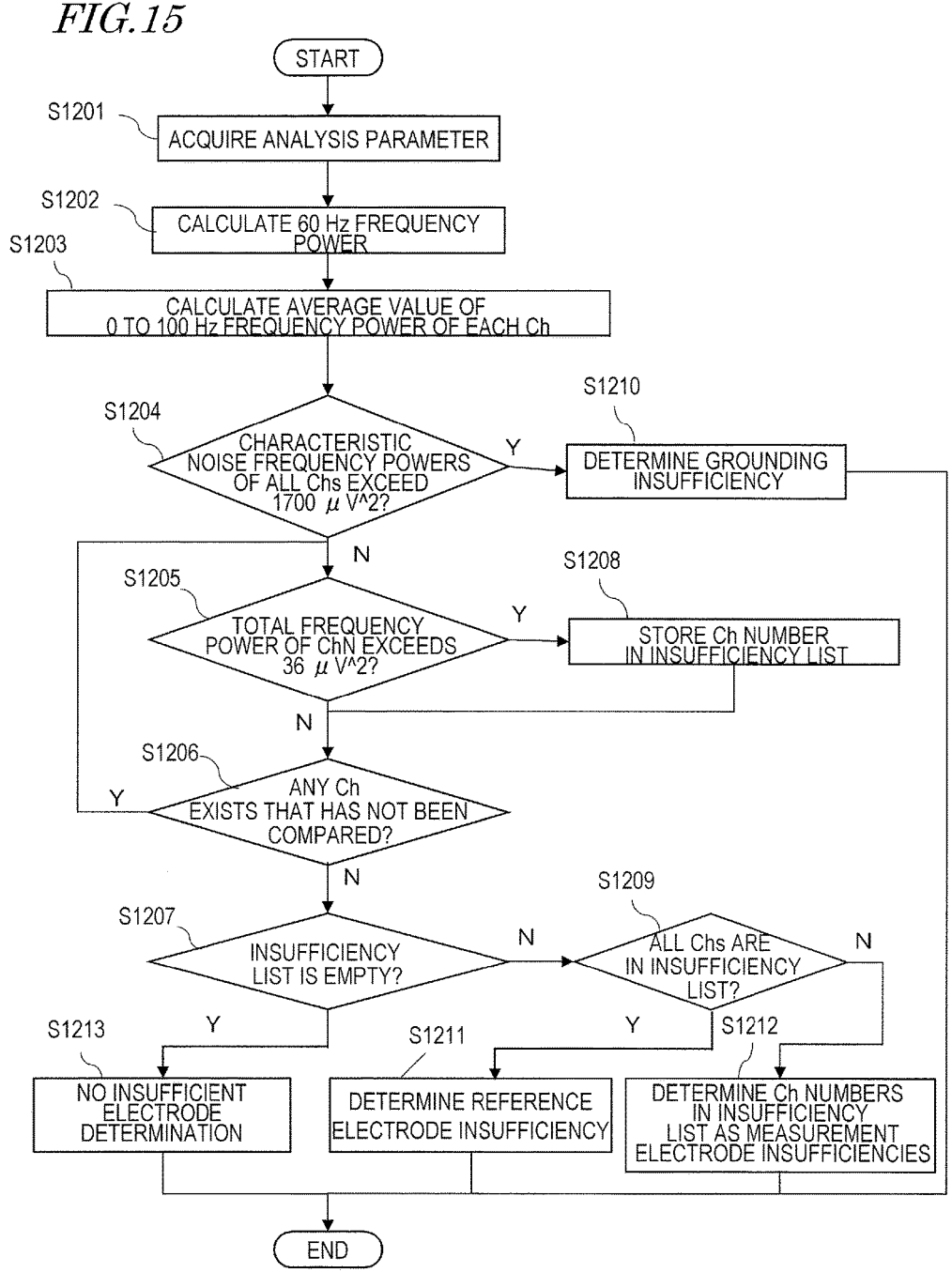

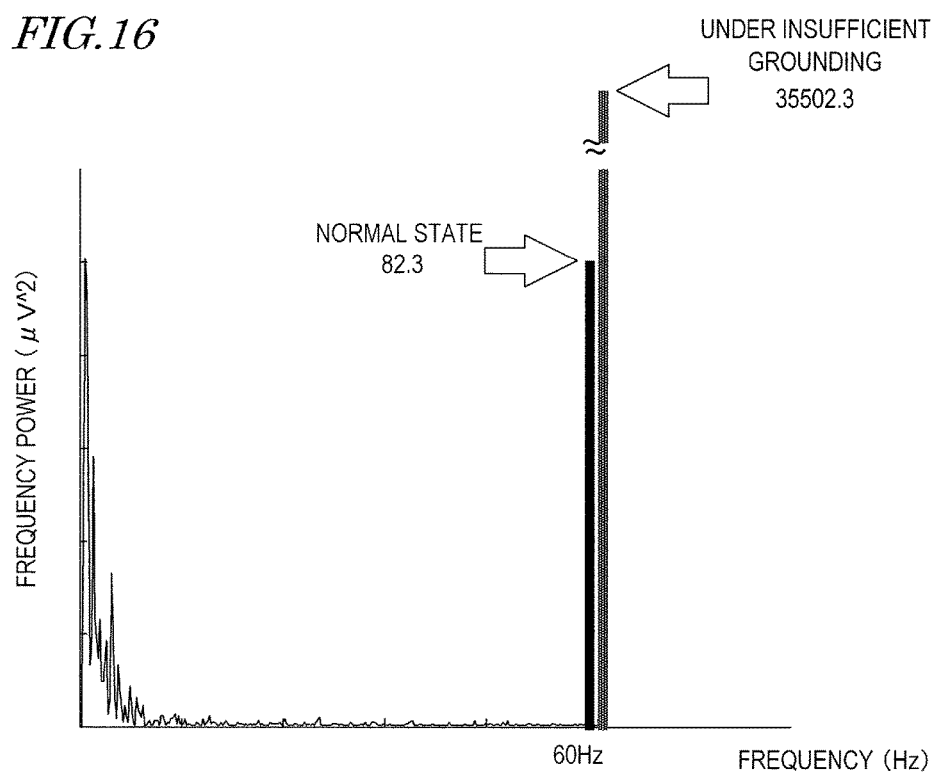

FIG.25

| ELECTRODE NUMBER | USAGE TYPE | COORDINATES | STATE |
|---|---|---|---|
| 1 | | 0,0,0 | NORMAL |
| 2 | | 0,-4,0 | NORMAL |
| 3 | MEASUREMENT ELECTRODE | 0,-2,0 | INSUFFICIENT |
| 4 | MEASUREMENT ELECTRODE | 0,2,0 | NORMAL |
| 5 | | 0,4,0 | NORMAL |
| 6 | | -2,-1,0 | NORMAL |
| 7 | GROUND | -2,1,0 | NORMAL |
| 8 | | 0,7,10 | NORMAL |
| 9 | | -1,7,12 | NORMAL |
| 10 | REFERENCE ELECTRODE | -3,7,12 | NORMAL |

ELECTRODE ATTACHMENT STATE DETERMINATION SYSTEM, ELECTRODE ATTACHMENT STATE DETERMINATION METHOD, AND PROGRAM THEREOF

This is a continuation of International Application No. PCT/JP2010/006828, with an international filing date of Nov. 22, 2010, which claims priority of Japanese Patent Application No. 2009-283678, filed on Dec. 15, 2009, the contents of which are hereby incorporated by reference.

BACKGROUND OF THE INVENTION

1. Field of the Invention

The present invention relates to a technique of, in an electroencephalogram measurement system which determines a state or intent of a user from a characteristic signal of the electroencephalogram of the user and feeds back the result of determination, determining a state of attachment of the electrodes which are utilized for electroencephalogram measurement.

2. Description of the Related Art

Conventionally, medical institutions have utilized electroencephalograms for diagnosis of epilepsy, Alzheimer's disease, and the like. On the other hand, there have been attempts at developing an electroencephalogram interface for inferring the psychological state of a healthy user based on his or her electroencephalogram and inferring his or her intent of manipulation or intent of selection with respect to a device.

For example, as an electroencephalogram interface for use with a healthy user, Japanese Laid-Open Patent Publication No. 7-108848 discloses an "apparatus for preventing drowsy driving" which infers the state of a user. The electroencephalogram interface of Japanese Laid-Open Patent Publication No. 7-108848 subjects an electroencephalogram to a frequency analysis and determines the user's drowsiness from the frequency power of an α wave component (8 Hz to 13 Hz)(see paragraph [0010]). In "The Mental Prosthesis Assessing the Speed of a P300-Based Brain-Computer Interface", TRANSACTIONS ON REHABILITATION ENGINEERING 2000, Vol. 8, June 2000 (herein referred to as "Non-Patent Document", Emanuel Donchin et al. also propose an interface for inferring an intent of selection of a user. Among event-related potentials of the electroencephalogram, the interface of the Non-Patent Document uses a characteristic signal called P300 to distinguish an option that a user wishes to select.

In the traditional electroencephalogram measurements mentioned above, a highly electrically conductive cream, called "paste", is applied on the electrodes, and someone else (not the user) needs to ensure that the electrodes are in tight contact with the skin (scalp) of the user.

Such manners of use, which require use of paste or help of someone else for wearing ease, will present burdens to the user an electroencephalogram interface is to be used in a daily-life environment. Now, an example will be discussed where an electroencephalogram measurement apparatus is incorporated in a wearable device such as a head-mount display (Head-Mount-Display: HMD) to measure an electroencephalogram for an electroencephalogram interface. Upon using an HMD, a user needs to be able to wear the electroencephalogram measurement apparatus together with the HMD at the same time. Moreover, the act of applying paste onto the electrodes also presents a burden on the user. Furthermore, after the device is detached, the paste will remain where the electrodes have been placed, and thus needs to be wiped off by the user himself or herself.

Therefore, in order for the user to easily wear an electroencephalogram measurement device by himself or herself, it is preferable to adopt electrodes which do not require use of paste (hereinafter referred to as "dry electrodes").

However, use of dry electrodes presents a problem in wearing stability. As one example, when a force acts on a dry electrode, the state of contact between the skin and the dry electrode will change because there is no paste. As a result, problems may occur, such as the electrode position changing even though contact with the skin may be maintained ("electrode shifting"), or a space being created between the skin and the electrode to disable electroencephalogram measurement ("lifting", "disengagement"). Note that a paste has a high viscosity, and serves not only to enhance the electrical conductivity between the skin and the electrode but also to prevent electrode shifting and electrode disengagement. This produces an effect of conserving the state of contact between the skin and the electrode even when the position of an electrode slightly is changed due to a force acting thereupon, because the paste with a high viscosity will then be deformed.

When electrode shifting occurs, the skin will be rubbing against the electrode surface, so that noises may likely be mixed. If an electrode disengagement occurs, electroencephalogram measurement will be so affected that it may not be continued. Since the user will not always be in a resting state but will undergo various motions in a daily-life environment, insufficiencies concerning electrode contact, such as electrode shifting and electrode disengagement, are probably likely to occur.

Therefore, when any insufficiency such as electrode shifting or electrode disengagement occurs, it is necessary to quickly detect that a situation obstructing electroencephalogram measurement has occurred.

Conventionally known methods for detecting electroencephalogram measurement insufficiencies are the methods in Japanese Examined Utility Model Publication No. 7-3347, Japanese Laid-Open Patent Publication No. 2006-212348, and Japanese Laid-Open Patent Publication No. 2006-6665 described below.

In Japanese Examined Utility Model Publication No. 7-3347, a weak current is allowed to flow through an electroencephalogram electrode, and a resistance value (contact resistance) between the skin and the electrode is calculated from the measured voltage value. As a result, the state of contact between the skin and the electrode is estimated, insufficiencies concerning the state of electrode attachment can be detected (see page 3, left column, second paragraph).

In Japanese Laid-Open Patent Publication No. 2006-212348, FIG. 2 shows that a coil is provided near an electrode, and that a voltage is applied to the coil. Based on whether a resultant induced current in the electrode is superposed on the electroencephalogram waveform or not, it is possible to determine whether the electrode and the scalp are in contact (paragraph [0038]).

In Japanese Laid-Open Patent Publication No. 2006-6665, measurements are taken of a plurality of "electroencephalogram channels", each electroencephalogram channel defining an electroencephalogram signal to be measured based on the potential difference between a pair of electrodes. In other words, a plurality of pairs of electrodes are provided, and an electroencephalogram signal is measured by each pair. Then, for each electroencephalogram channel, S (i.e., the signal to be measured) and N (i.e., any signal other than the signal to be measured) are calculated. Through a comparison of the S/N ratio against a threshold value, it is determined as to which electroencephalogram channel is suffering from a measurement insufficiency (paragraph [0028]).

Japanese Laid-Open Patent Publication No. 2006-14833 discloses cerebral function judging system 1. The cerebral function judging system 1 judges the contact state of each electrode 2 of the brain wave signal primary detecting element 3. After having judged that a contact state is fine, the system conducts cerebral function analysis. Thus, a cerebral function state can be judged with sufficient accuracy. Since the system does not start inspections before having judged that a contact state is fine, the system can prevent from reducing analysis accuracy of cerebral function state or spoiling inspection results before the system starts the inspection (paragraph [0020]).

However, any of the techniques of the aforementioned conventional approaches has a problem of being unable to identify which electrode is suffering from an insufficiency in the electroencephalogram measurements in a daily-life environment. The respective problems of the above techniques will be described in detail below.

Firstly, in the approach of Japanese Examined Utility Model Publication No. 7-3347, it is necessary to stop the electroencephalogram measurement before measuring the contact resistance. However, this approach is based on the premise that the state of contact of an electrode will not change very much, such that once a contact resistance is measured at the beginning of measurement, there is no need to take more measurements. Accordingly, no thoughts are given to the reconciliation between electroencephalogram measurements and contact resistance measurements. However, the state of electrode attachment will change over time in a daily-life environment, and thus the frequency with which to confirm the state of attachment should increase, but stopping the electroencephalogram measurement each time before a contact resistance measurement will be considerably inconvenient.

In the approach of Japanese Laid-Open Patent Publication No. 2006-212348 of determining whether an electrode is in contact with the skin or not, no consideration is given to the insufficiencies concerning the state of contact of the electrode, e.g., shifting of the electrode that may occur in response to the user's motion, or changes in the pressure from the electrode.

Thus, in Japanese Examined Utility Model Publication No. 7-3347, and Japanese Laid-Open Patent Publication No. 2006-212348, no consideration is given to the detection of insufficient electrodes in an environment where the state of electrode attachment may change, making it difficult to identify which electrode has become insufficient.

On the other hand, in Japanese Laid-Open Patent Publication No. 2006-6665, insufficiencies of electroencephalogram measurement can also be detected even in an environment where the state of attachment may change. However, it is still impossible to identify which electrode is suffering from insufficient wearing.

Note that, even by using paste, electrode shifting and electrode disengagement cannot be completely eliminated. Therefore, the above-described problems of the conventional techniques are not confined to dry electrodes alone. Also in the case where electrode shifting or electrode disengagement occurs in an electrode where paste is applied, it is still necessary to identify which electrode has become insufficient.

SUMMARY OF THE INVENTION

The present invention has been made in view of the above problems, and an objective thereof is to, in electroencephalogram measurements to be taken in a daily-life environment, detect an insufficiency in electrode attachment, and identify which one of a plurality of electrodes has become insufficient, thus enabling stable electroencephalogram measurements.

An electrode attachment state determination system according to the present invention comprises: an electroencephalogram measurement section for measuring an electroencephalogram signal of a user by using at least one set of electrodes, the set including a ground electrode, a reference electrode, and a measurement electrode; a frequency analysis section for performing a frequency analysis of the electroencephalogram signal; an insufficient electrode determination section for extracting at least one parameter of a total frequency power and a noise amount from a result of the frequency analysis, and through a comparison of a value of the at least one parameter against a predetermined threshold value, determining whether the ground electrode, the reference electrode, or the measurement electrode has an insufficient state of attachment; and an output section for, when an insufficient state of attachment is determined, presenting information indicating the insufficient state of attachment of the electrode to the user.

The insufficient electrode determination section may extract the noise amount parameter from the result of the frequency analysis, and if the noise amount parameter has a value exceeding a predetermined first threshold value, determine that the ground electrode has an insufficient state of attachment.

The insufficient electrode determination section may further extract the total frequency power parameter from the result of the frequency analysis, and if the total frequency power parameter has a value exceeding a predetermined second threshold value, determine that one of the reference electrode and the measurement electrode has an insufficient state of attachment.

The electroencephalogram measurement section may use a plurality of sets of electrodes each including a ground electrode, a reference electrode, and a measurement electrode, to measure an electroencephalogram signal with each set; the frequency analysis section may perform a frequency analysis of each electroencephalogram signal; and the insufficient electrode determination section may extract a noise amount parameter from a result of the frequency analysis of each electroencephalogram signal, and if all of the extracted noise amount parameters have values exceeding a predetermined first threshold value, determine that the ground electrode has an insufficient state of attachment, and extract a total frequency power parameter from the result of the frequency analysis of each electroencephalogram signal, and if all of the extracted total frequency power parameters have values exceeding a predetermined second threshold value, determine that the reference electrode has an insufficient state of attachment, or if some of the extracted total frequency power parameters have values exceeding the second threshold value, determine that the measurement electrode has an insufficient state of attachment.

The electroencephalogram measurement section may measure a first potential difference between the ground electrode and the reference electrode and a second potential difference between the ground electrode and the measurement electrode, and measure the electroencephalogram signal based on a difference between the second potential difference and the first potential difference.

A noise being steadily mixed from an external environment at a previously identified frequency may be superposed on the electroencephalogram signal; and from the result of the frequency analysis, the insufficient electrode determination section may extract a frequency power of the noise as the noise amount parameter.

The previously identified frequency may be a frequency of a commercial-power noise of a device which is in the external environment.

As the total frequency power parameter, the insufficient electrode determination section may extract an average value of a power of the electroencephalogram signal in an analyzable frequency band.

The electrode attachment state determination system may further comprise an electrode restoration determination section for determining, based on a signal measured by using an insufficient electrode which is determined as having an insufficient state of attachment, whether the insufficiency in the state of attachment of the insufficient electrode has been eliminated or not, wherein, when the insufficient electrode is the ground electrode, the electrode restoration determination section may extract the noise amount parameter from the result of the frequency analysis of the signal as measured by using the insufficient electrode, and, if the noise amount parameter has a value exceeding a predetermined third threshold value, the electrode restoration determination section may determine that the insufficiency in the state of attachment of the insufficient electrode has not been eliminated, or if the noise amount parameter does not have a value exceeding a predetermined third threshold value, the electrode restoration determination section may determine that the insufficiency in the state of attachment of the insufficient electrode has been eliminated.

The electrode attachment state determination system may further comprise an electrode restoration determination section for determining, based on a signal measured by using an insufficient electrode which is determined as having an insufficient state of attachment, whether the insufficiency in the state of attachment of the insufficient electrode has been eliminated or not, wherein, when the insufficient electrode is one of the reference electrode and the measurement electrode, the electrode restoration determination section may calculate an average value and variance of the signal as measured by using the insufficient electrode, and, if both of the average value and the variance are zero, the electrode restoration determination section may determine that the insufficiency in the state of attachment of the insufficient electrode has not been eliminated, or if not both of the average value and the variance are zero, the electrode restoration determination section may determine that the insufficiency in the state of attachment of the insufficient electrode has been eliminated.

The electrode attachment state determination system may further comprise a measurement electrode replacement section for, based on prestored electrode information, replacing an insufficient electrode which is determined as having an insufficient state of attachment with a replacing electrode, wherein, the electrode information may describe information of a type and position of each of electrodes which are available for measuring an electroencephalogram signal of the user; with respect to an insufficient electrode which is determined as having an insufficient state of attachment, the measurement electrode replacement section may identify the type and position of the insufficient electrode, and refer to the electrode information to identify the replacing electrode based on electroencephalographic characteristics of an electroencephalogram signal to be measured by the insufficient electrode; and instead of the insufficient electrode, the electroencephalogram measurement section may use the identified replacing electrode to measure an electroencephalogram signal.

The electrode attachment state determination system may further comprise an electroencephalogram processing section for distinguishing an intent of the user by utilizing a characteristic component contained in the measured electroencephalogram signal, wherein, when the insufficient electrode is the measurement electrode, the measurement electrode replacement section may refer to the electrode information to identify, as the replacing electrode, an electrode which is within a predetermined distance from the insufficient electrode and which is at a closest distance from a brain position where the characteristic component of the electroencephalogram signal is generated.

The electrode attachment state determination system may further comprise an electroencephalogram processing section for distinguishing an intent of the user by utilizing a characteristic component contained in the measured electroencephalogram signal, wherein, when the insufficient electrode is the reference electrode, the measurement electrode replacement section may refer to the electrode information to identify, as the replacing electrode, an electrode which is within a predetermined distance from a mastoid.

The electrode attachment state determination system may further comprise an electroencephalogram processing section for distinguishing an intent of the user by utilizing a characteristic component contained in the measured electroencephalogram signal, and executing a process which is in accordance with the intent of the user, wherein, from a result of the frequency analysis, the insufficient electrode determination section may extract at least one parameter of a total frequency power and a noise amount, and through a comparison of a value of the at least one parameter against a predetermined threshold value, determine a state of attachment of the ground electrode, the reference electrode, or the measurement electrode to be sufficient or insufficient; and if the state of attachment is determined to be insufficient, the output section may present information indicating the insufficient state of attachment of the electrode to the user, and if the state of attachment is determined to be sufficient, the output section may output a result of the process which is in accordance with the intent of the user.

An electrode attachment state determination method according to the present invention comprises the steps of: measuring an electroencephalogram signal of a user by using at least one set of electrodes including a ground electrode, a reference electrode, and a measurement electrode; performing a frequency analysis of the electroencephalogram signal; from a result of the frequency analysis, extracting at least one parameter of a total frequency power and a noise amount, and through a comparison of a value of the at least one parameter against a predetermined threshold value, determining whether the ground electrode, the reference electrode, or the measurement electrode has an insufficient state of attachment; and when an insufficient state of attachment is determined, presenting information indicating the insufficient state of attachment of the electrode to the user.

A computer program for determining a state of electrode attachment is to be executed by a computer, and causes the computer to execute the steps of: measuring an electroencephalogram signal of a user by using at least one set of electrodes including a ground electrode, a reference electrode, and a measurement electrode; performing a frequency analysis of the electroencephalogram signal; from a result of the frequency analysis, extracting at least one parameter of a total frequency power and a noise amount, and through a comparison of a value of the at least one parameter against a predetermined threshold value, determining whether the ground electrode, the reference electrode, or the measurement electrode has an insufficient state of attachment; and when an insufficient state of attachment is determined, presenting information indicating the insufficient state of attachment of the electrode to the user.

According to the present invention, in an electrode attachment state determination system in which electrodes are used, it is possible to detect insufficiencies in electrode attachment and identify which one of a plurality of electrodes has become insufficient, thus enabling stable electroencephalogram measurements.

Other features, elements, processes, steps, characteristics and advantages of the present invention will become more apparent from the following detailed description of preferred embodiments of the present invention with reference to the attached drawings.

Figure 2:
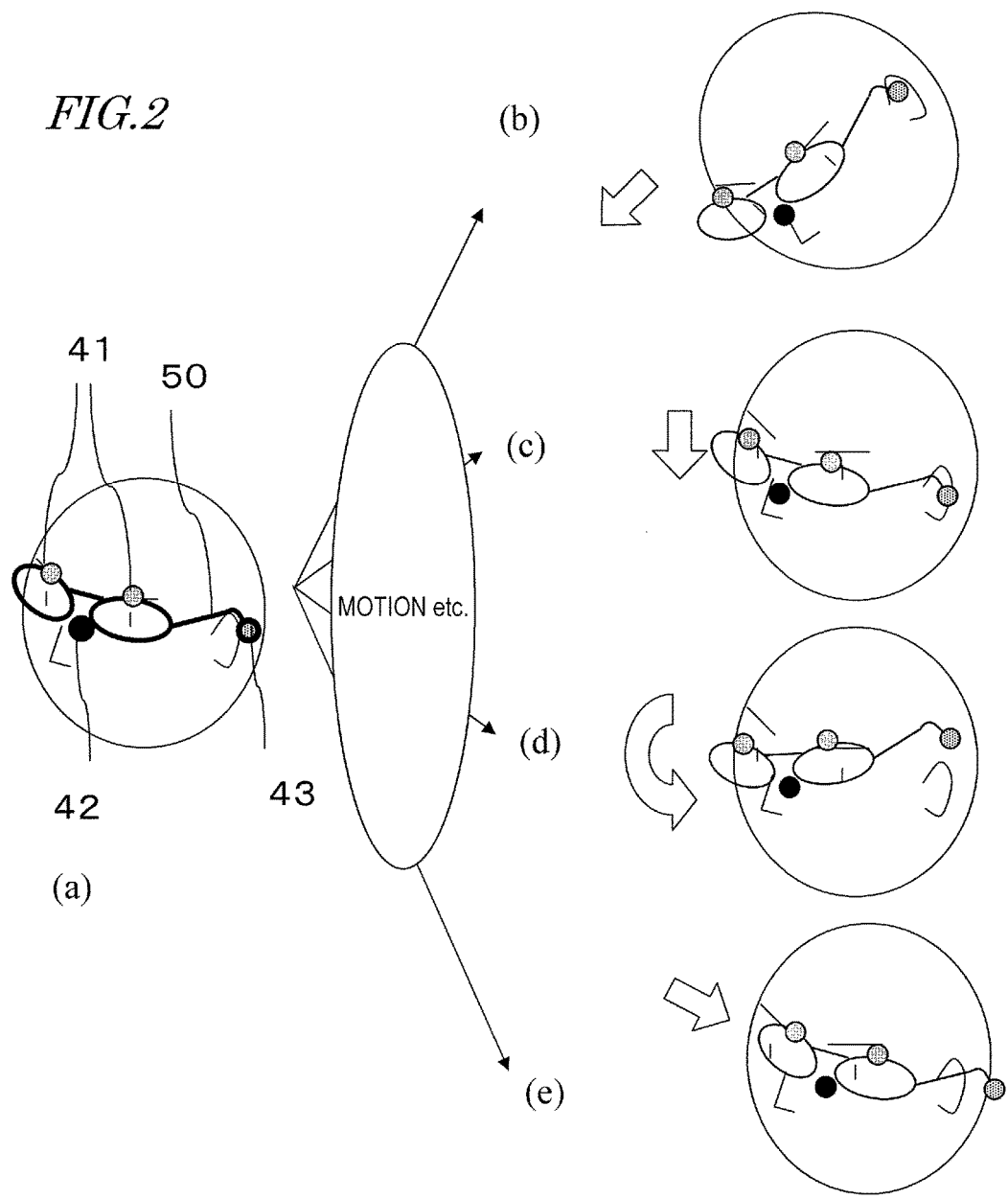

Portions (a) to (e) of FIG. 2 are diagrams showing an example of an eyeglass-type head-mount display (HMD) 50 in which dry electrodes for electroencephalogram measurement are incorporated, and their states of attachment.

Figure 3A:
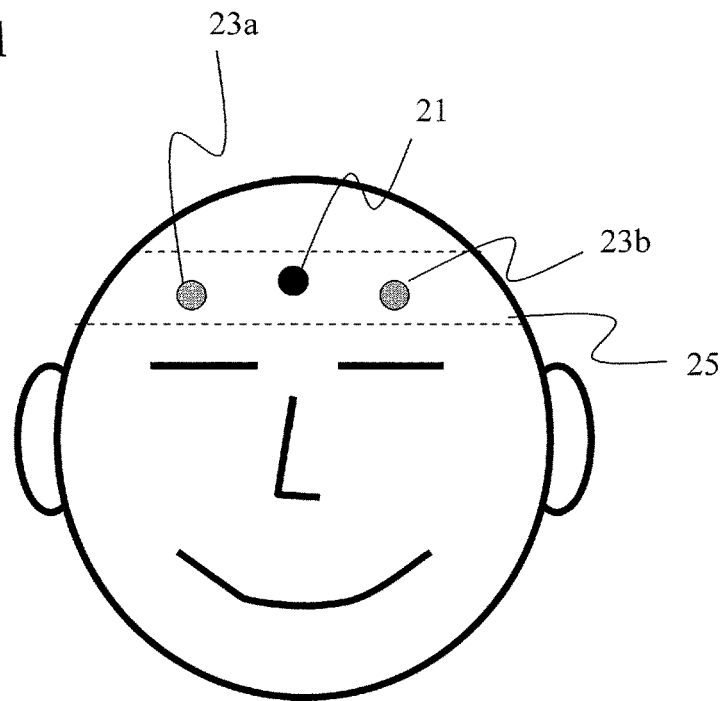
Figure 3B:
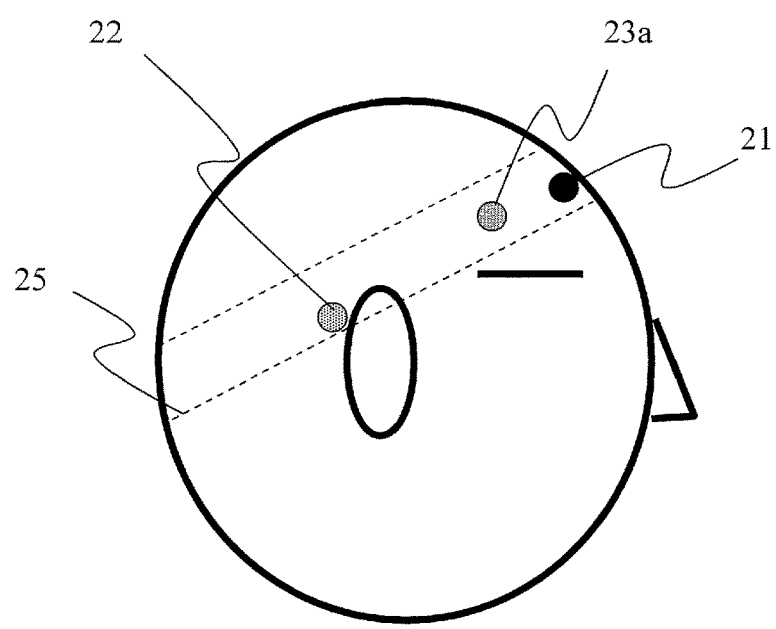

FIGS. 3A and 3B are diagrams showing positioning of electrodes which are provided within the range of the shape of an hair band 25 of an HMD.

Figures 4, 5:
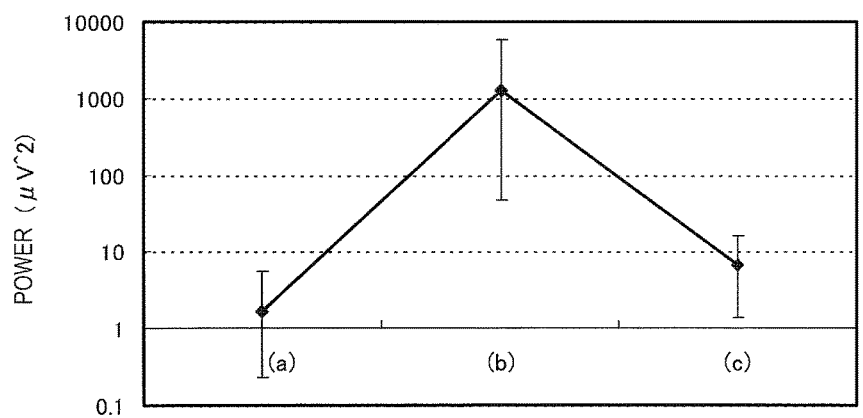

FIG. 4 is a diagram showing results of an electroencephalogram analysis.

FIG. 5 is a diagram showing an average value of amounts of mixed AC noise of all test subjects and an extent of variations among all test subjects, in the three states of: (a) a normal state; (b) disengaging the ground; and (c) disengaging a measurement electrode.

Figure 6:
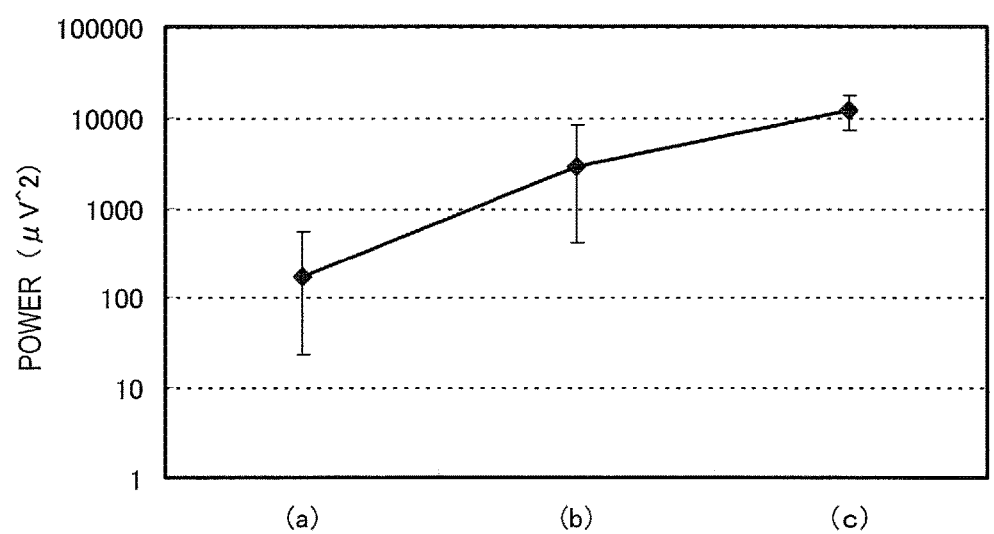

FIG. 6 is a diagram showing an average value of total frequency powers of all test subjects and an extent of variations among all test subjects in the three states of (a), (b), and (c).

Figure 7:
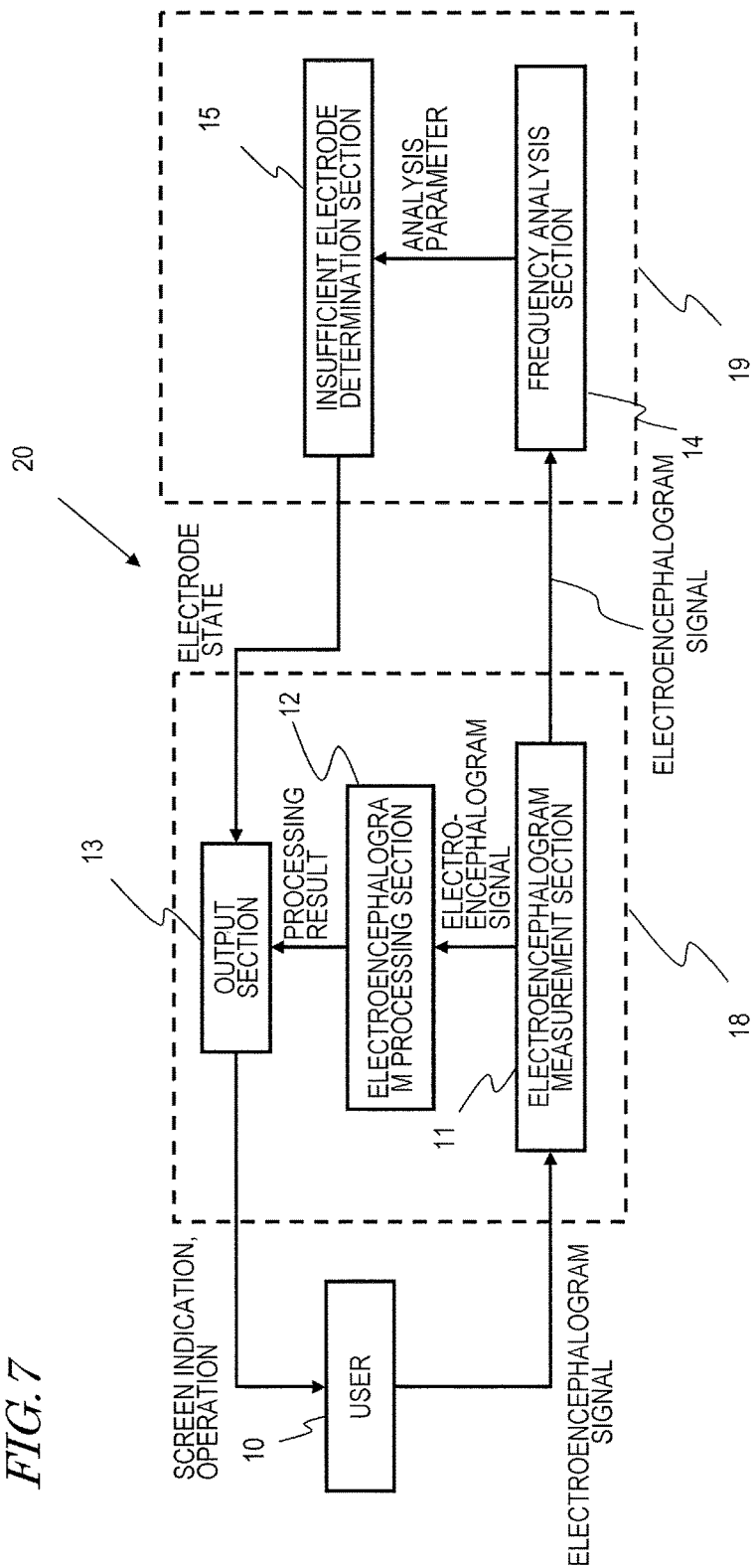

FIG. 7 is a diagram showing the functional block construction of an electrode attachment state determination system 20 of the present embodiment.

Figure 8:
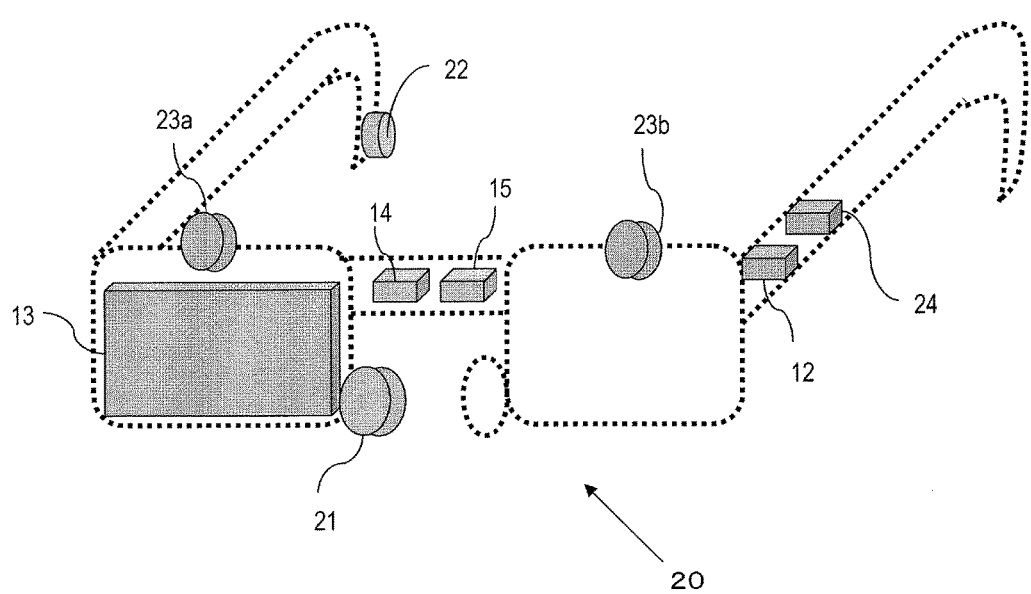

FIG. 8 is a diagram showing an exemplary shape of a device which embodies the electrode attachment state determination system 20 in the form of an HMD.

Figure 9:
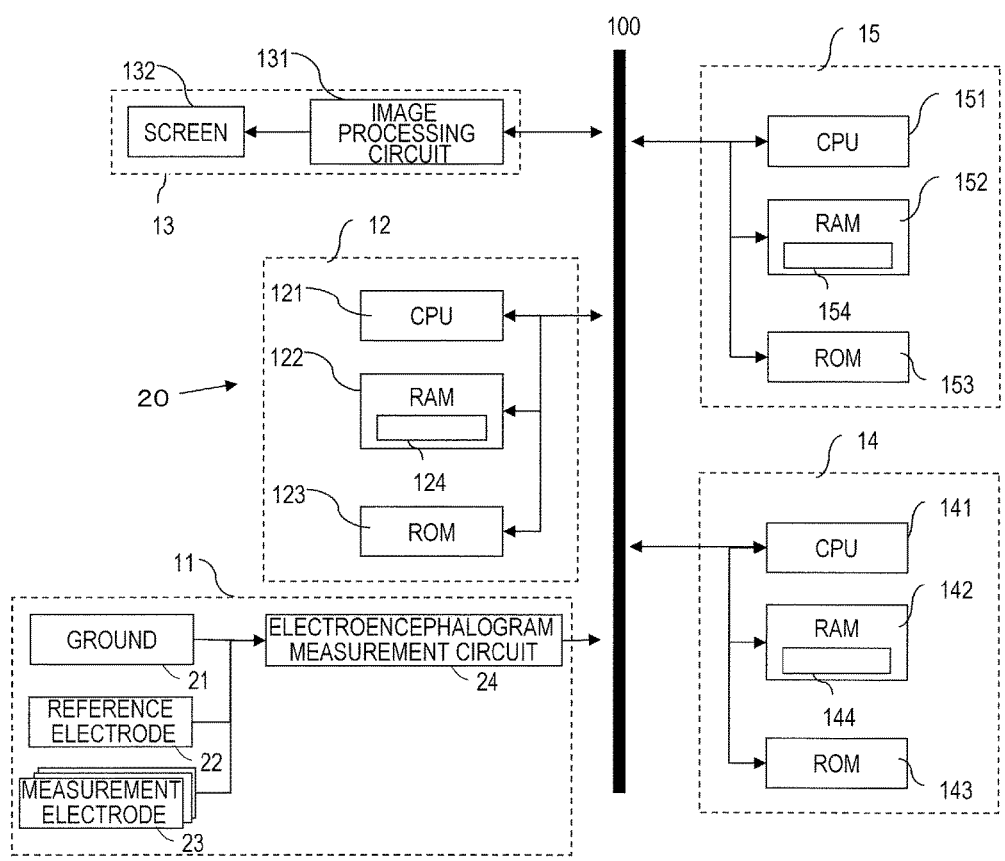

FIG. 9 is a diagram showing an exemplary hardware construction of the electrode attachment state determination system 20.

Figure 10:
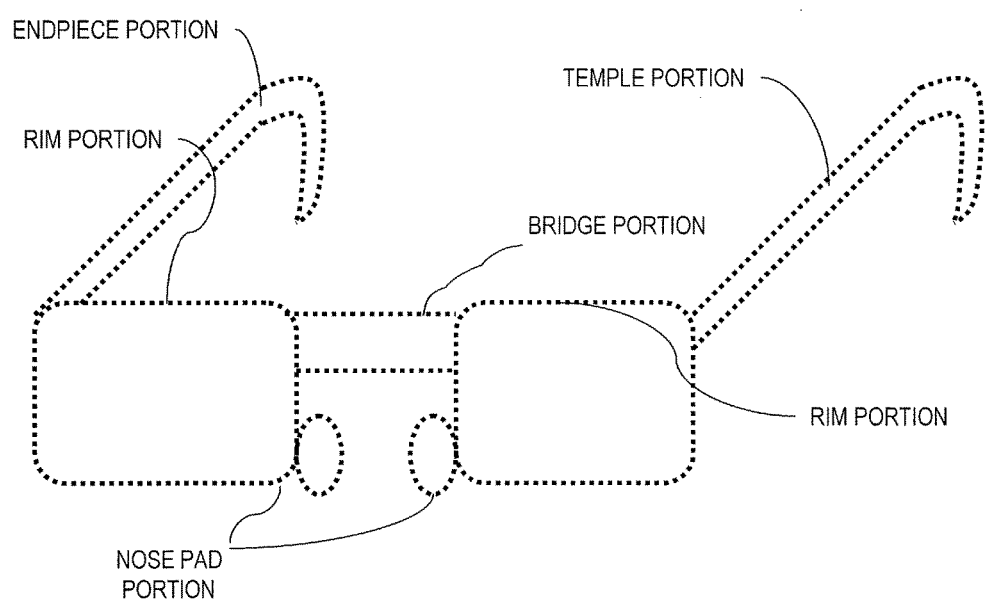

FIG. 10 is a diagram showing the names of the respective portions of eyeglasses.

Figure 11:
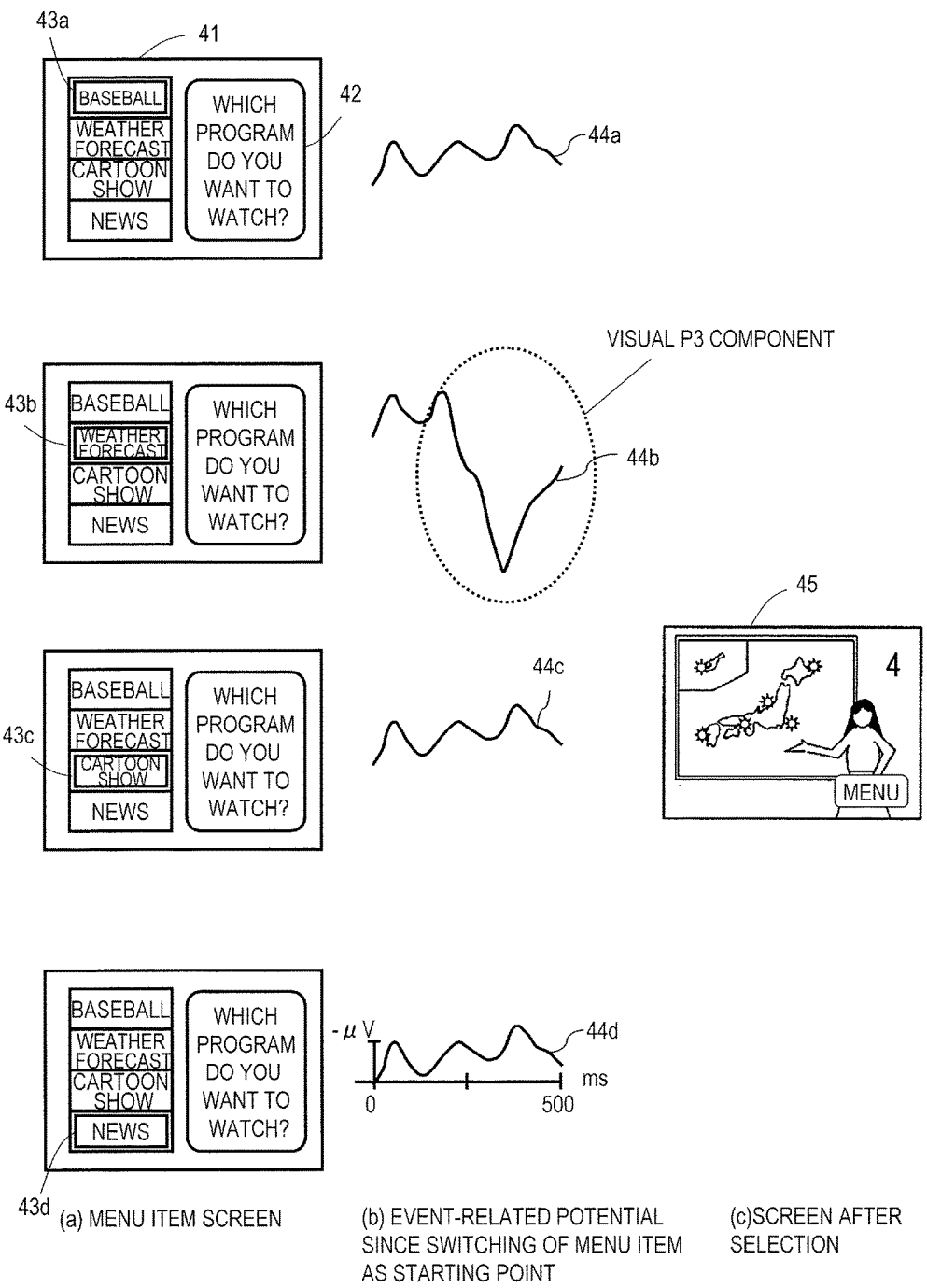

FIG. 11 is a diagram showing exemplary screens of an electroencephalogram interface.

Figure 12:
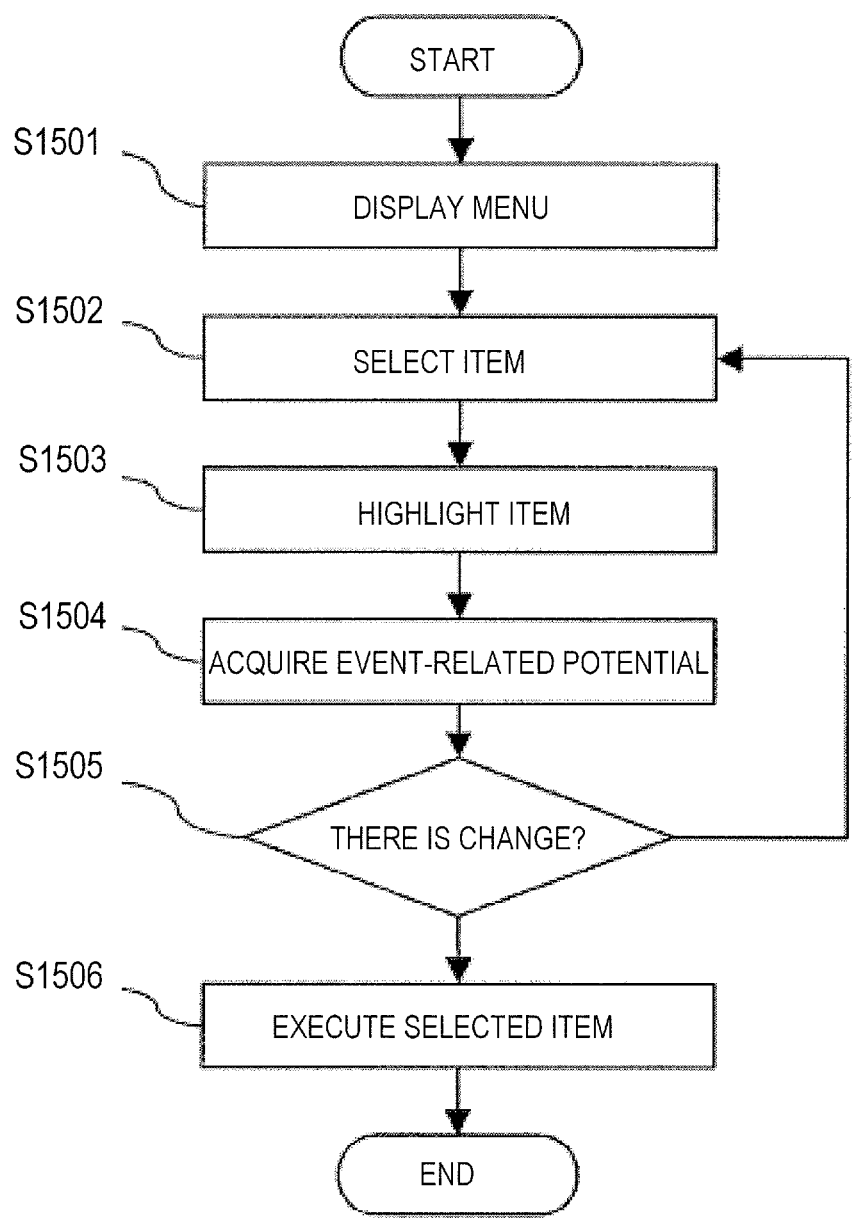

FIG. 12 is a flowchart showing a procedure of electroencephalogram interface processing by an electroencephalogram processing section 12.

Figure 13:
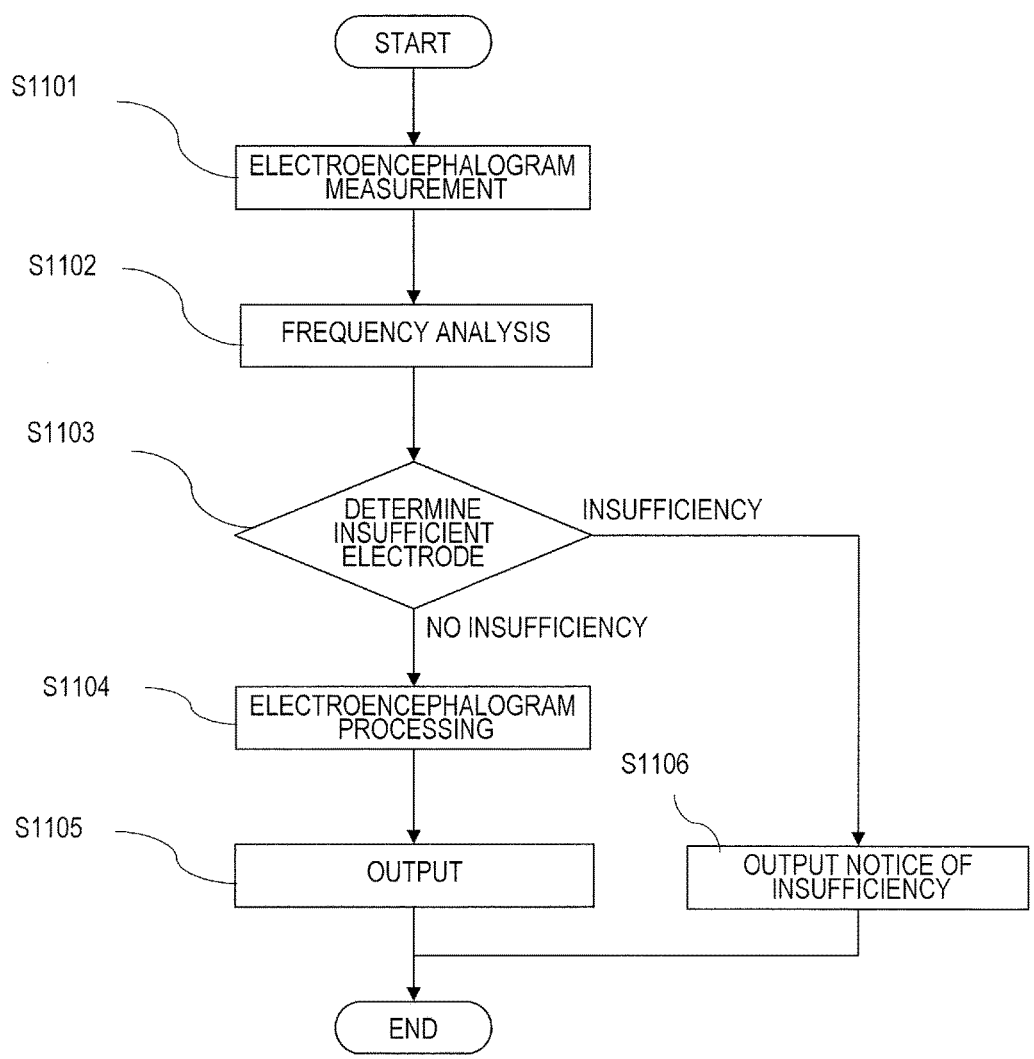

FIG. 13 is a flowchart showing the overall processing by the electrode attachment state determination system 20.

Figure 14:
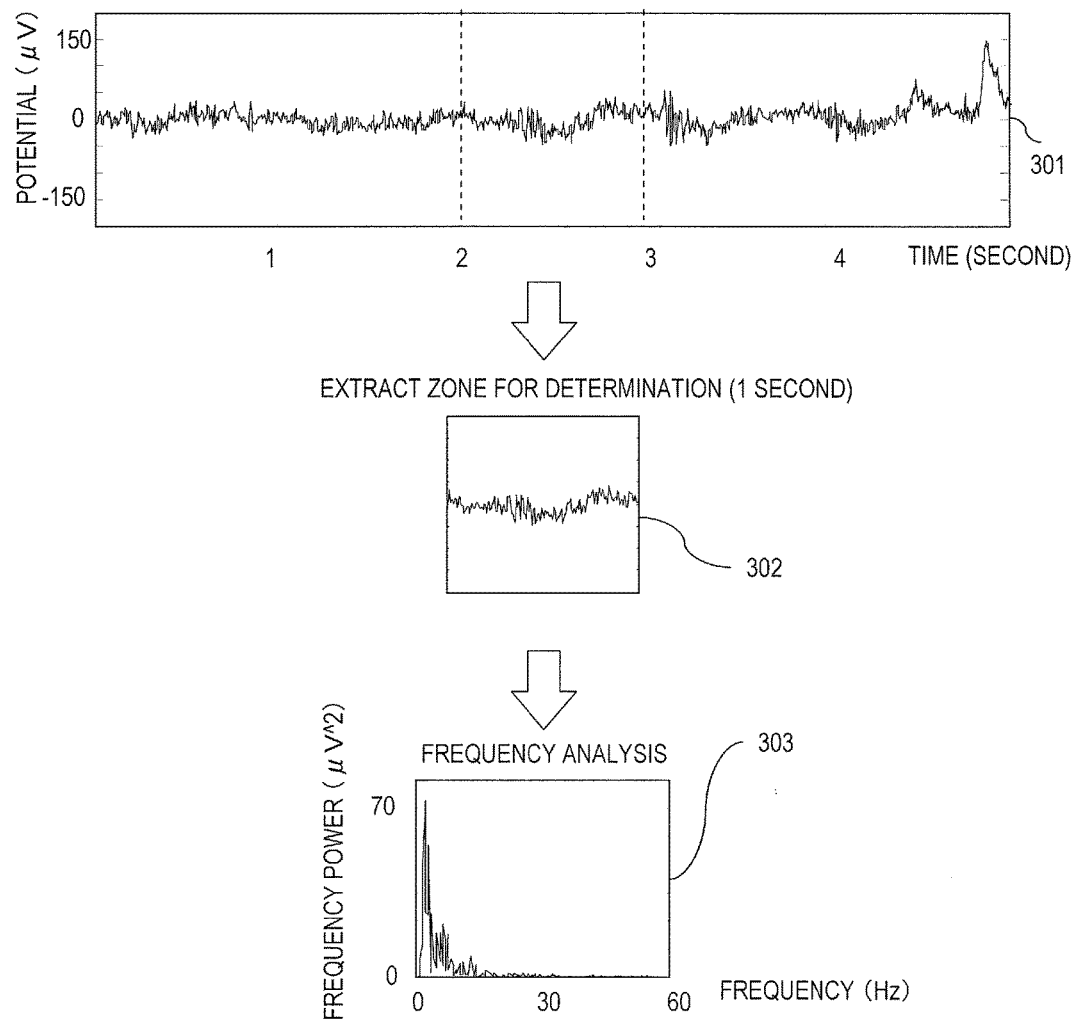

FIG. 14 is a diagram showing an exemplary electroencephalogram waveform for processing by a frequency analysis section 14.

FIG. 15 is a flowchart showing a detailed processing procedure of a process performed by an insufficient electrode determination section 15 at step S1103 in FIG. 13.

FIG. 16 is an exemplary graph representation of a frequency analysis result in the case where a ground 21 is normally worn (NORMAL) and a frequency analysis result in the case where the ground is disengaged (INSUFFICIENT GROUNDING).

Figure 17A:
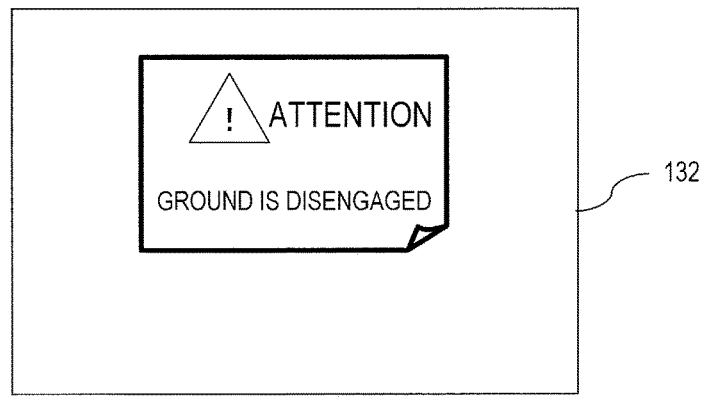
Figure 17B:
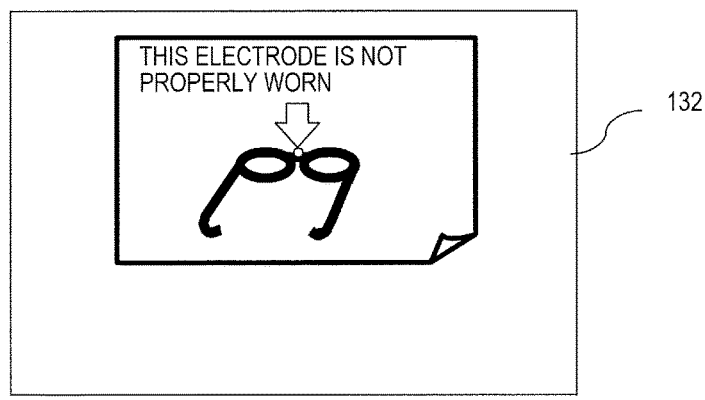
Figure 17C:
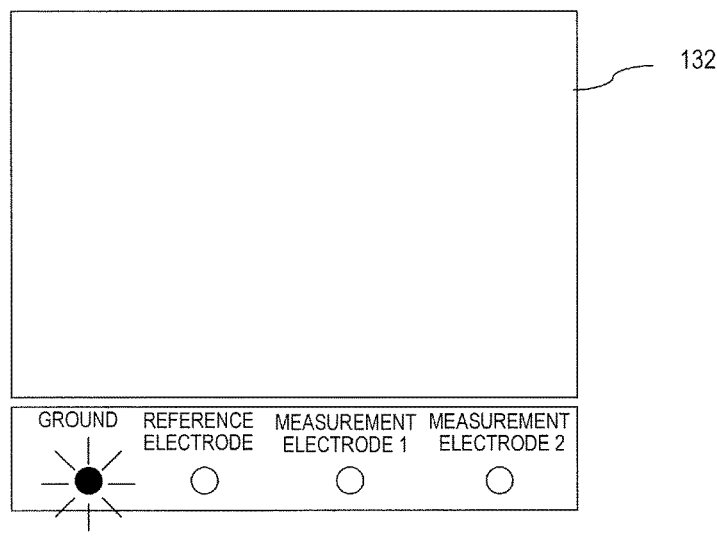

FIGS. 17A to 17C are diagrams showing examples of notices of insufficiency when an insufficient grounding determination is made.

Figure 18:
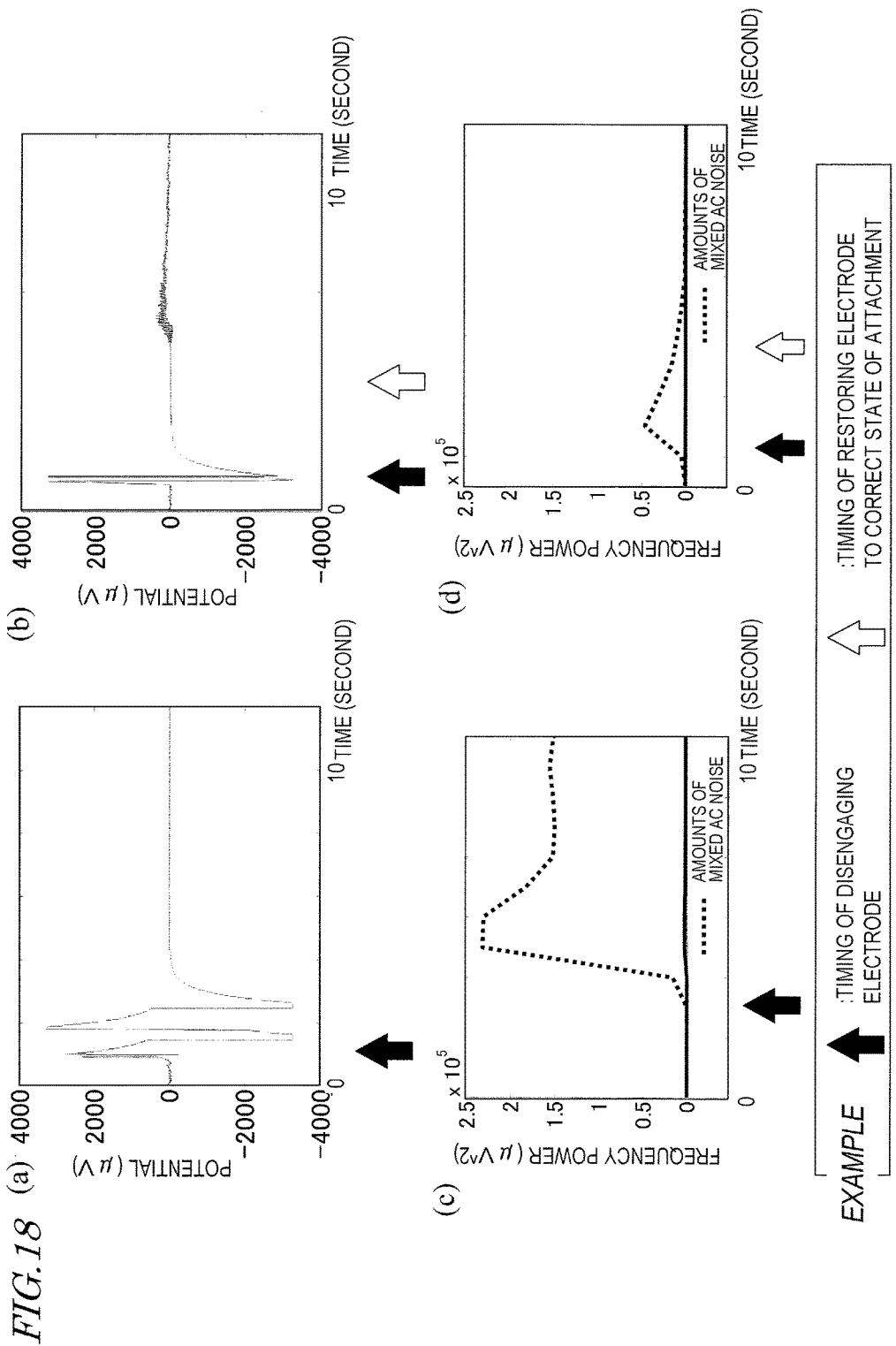

Portions (a) to (d) of FIG. 18 are graphs showing experimental results.

Figure 19:
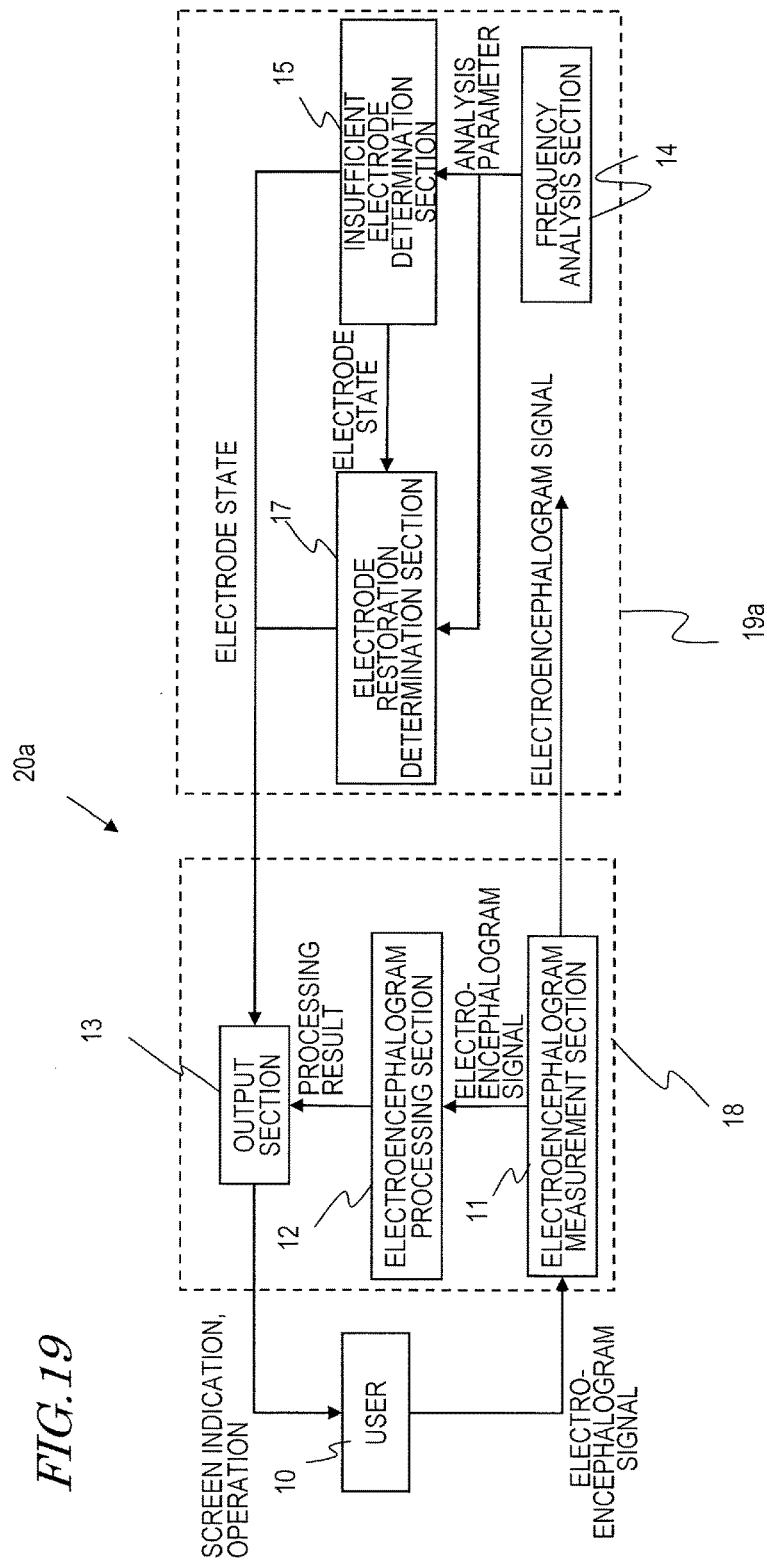

FIG. 19 is a diagram showing an electrode attachment state determination system 20a according to a variant of Embodiment 1.

Figure 20:
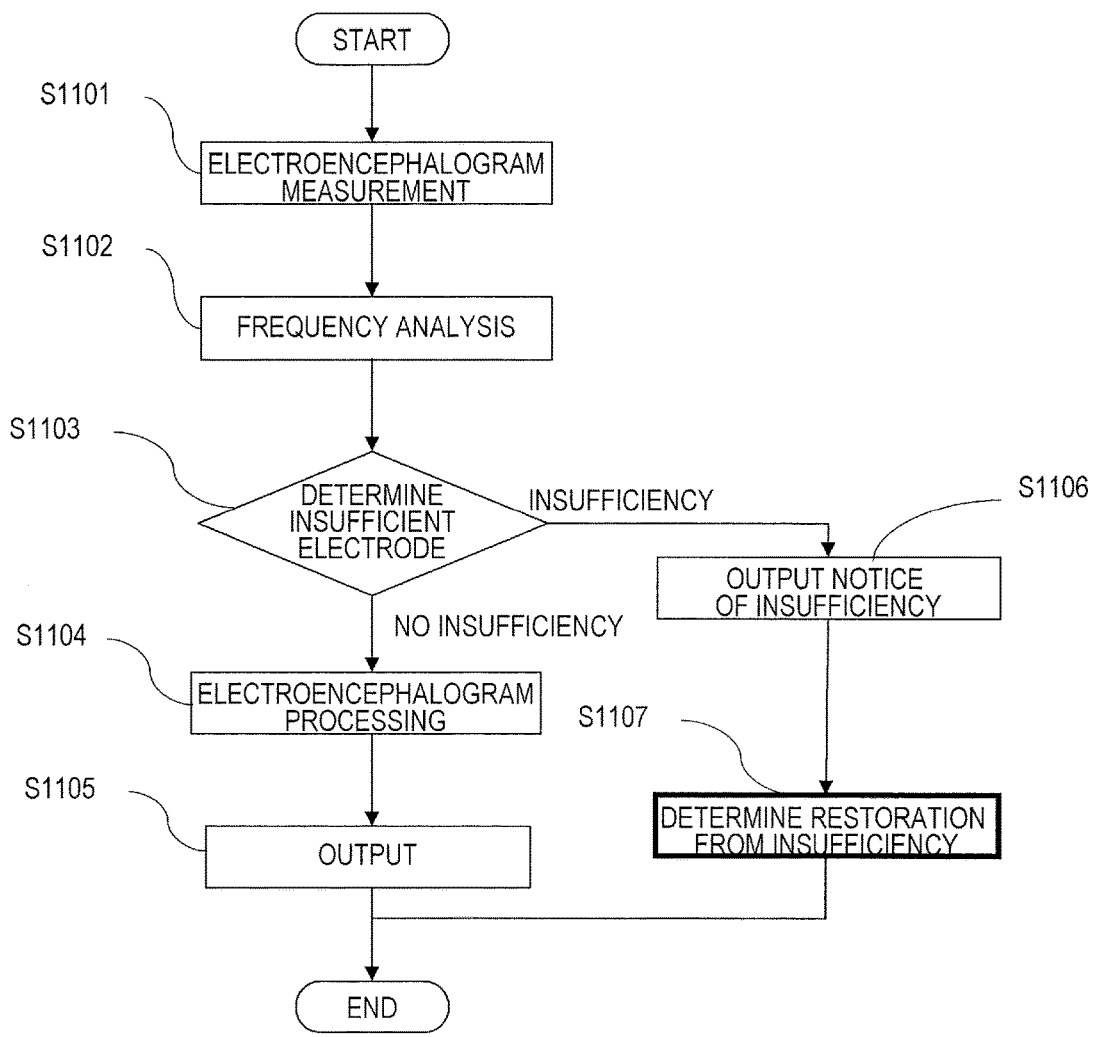

FIG. 20 is a flowchart showing a procedure of processing by an electrode attachment state determination system 20a, which additionally includes processing by an electrode restoration determination section 17.

Figure 21:
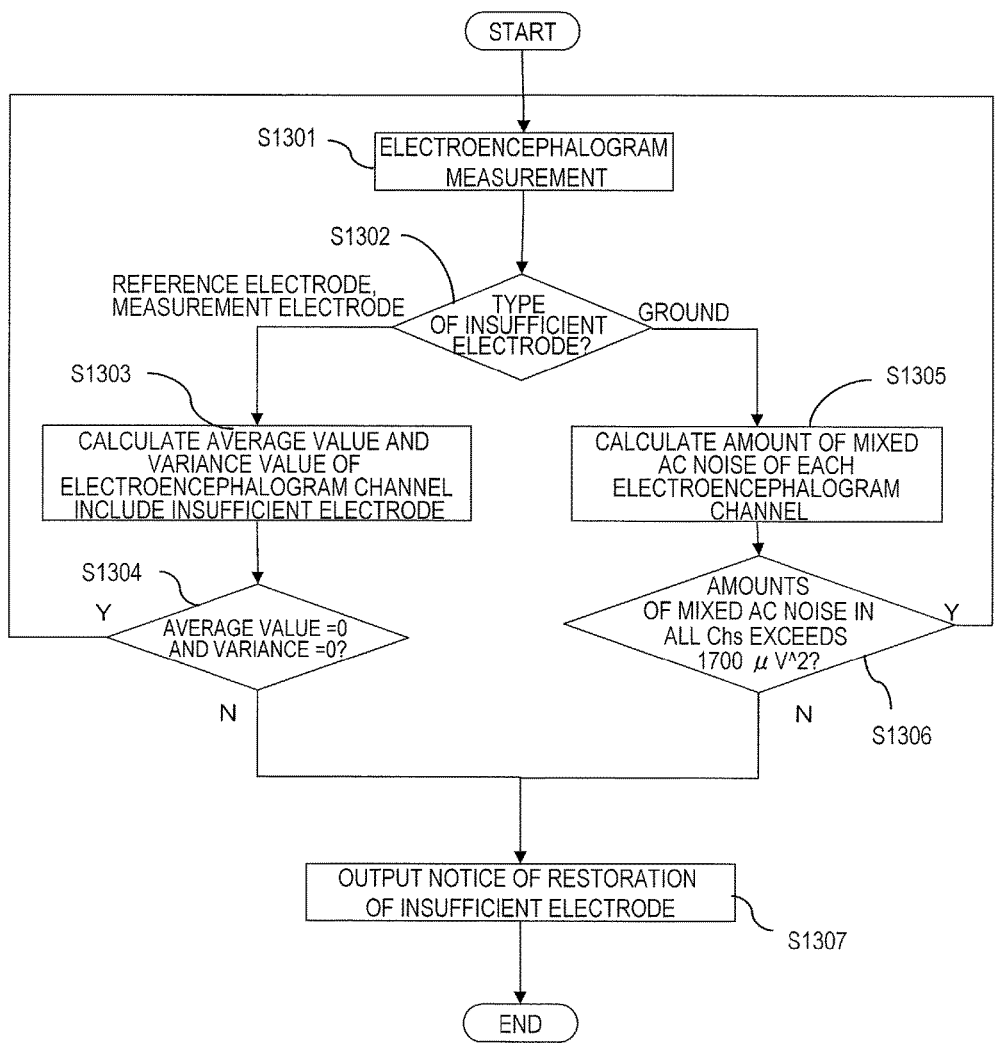

FIG. 21 is a flowchart for describing an electrode restoration determination process (step S1107 in FIG. 20) performed by the electrode restoration determination section 17.

Figure 22:
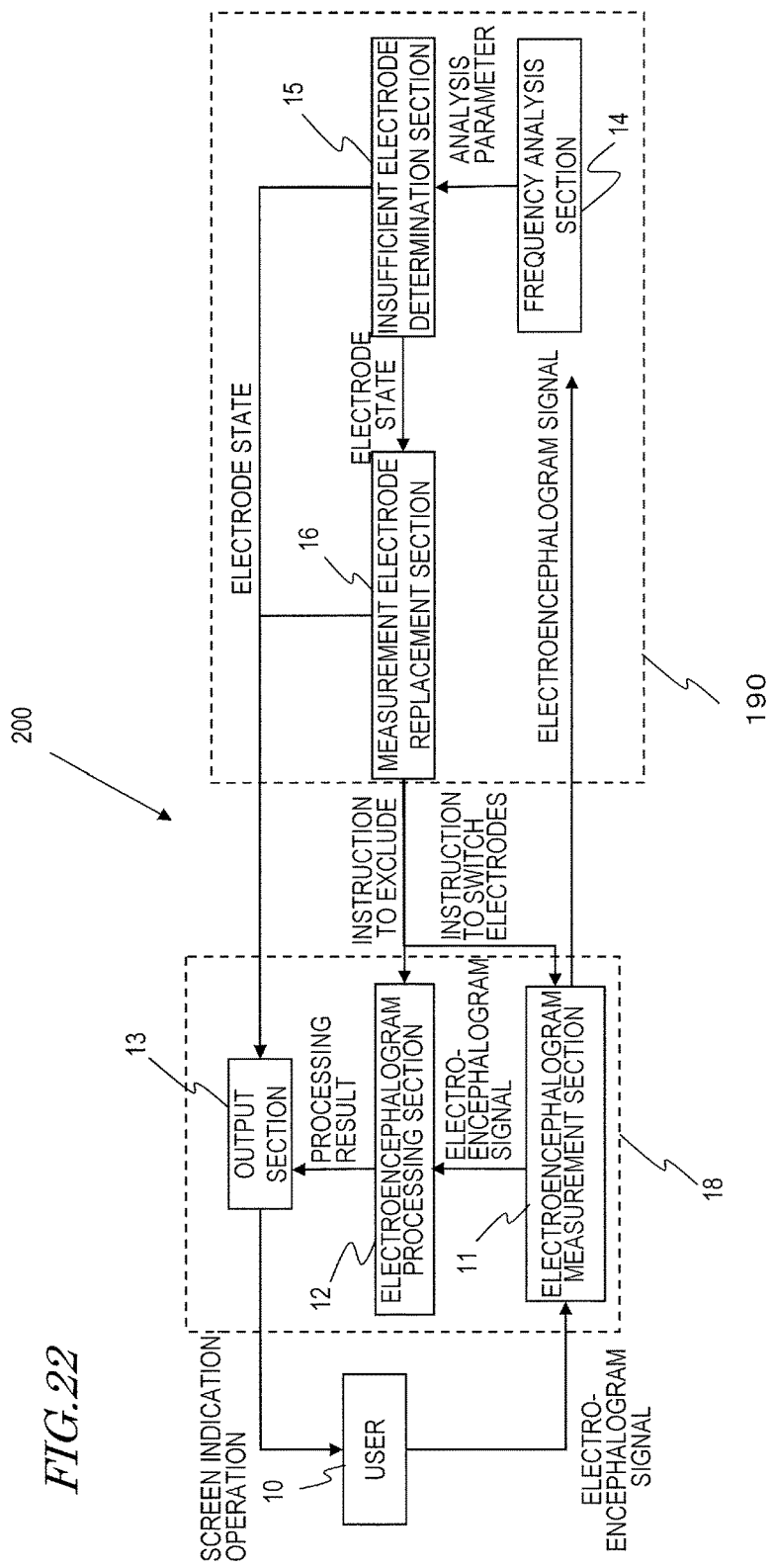

FIG. 22 is a diagram showing the functional block construction of an electrode attachment state determination system 200 according to Embodiment 2.

Figure 23:
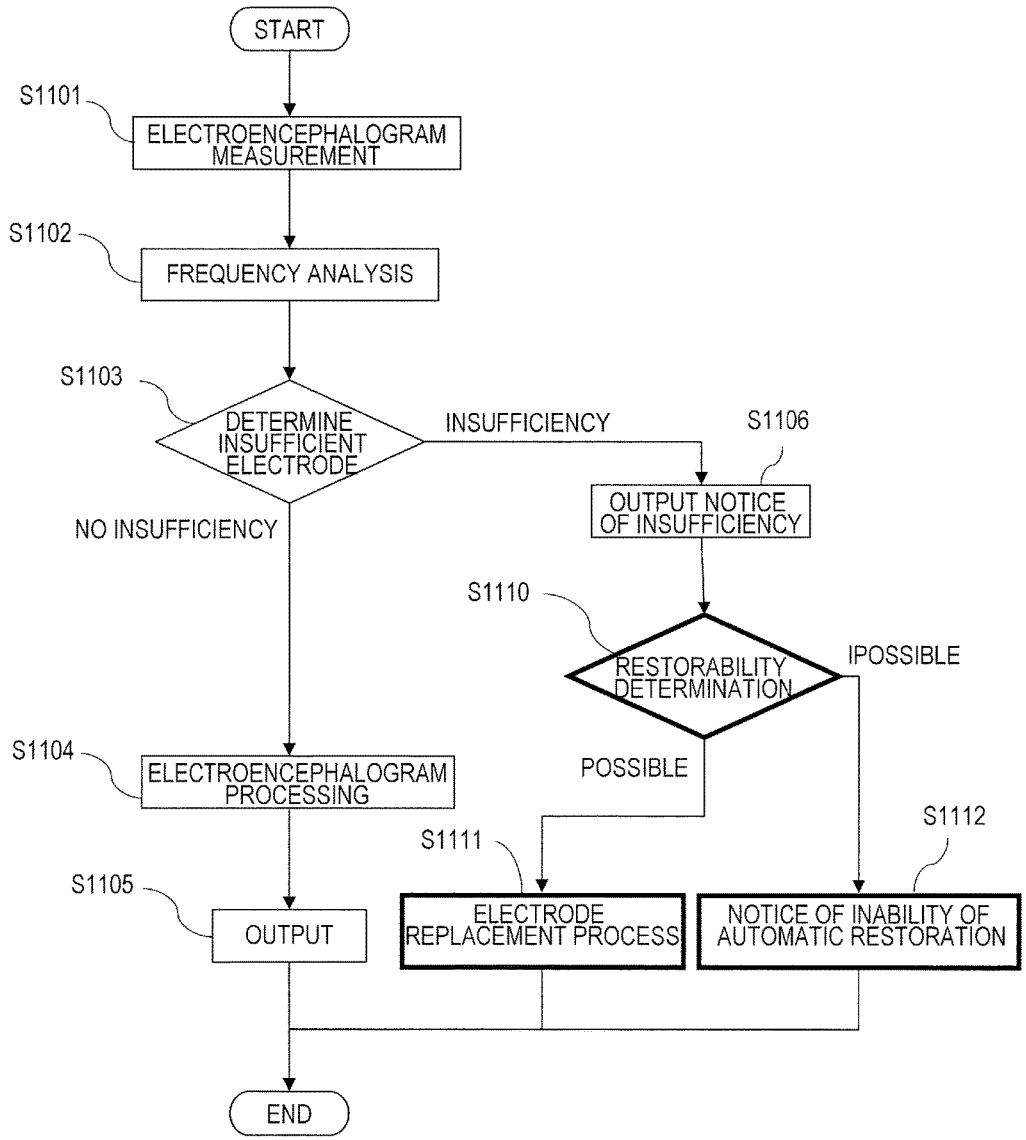

FIG. 23 is a flowchart showing a procedure of processing by the electrode attachment state determination system 200, which additionally includes processing by a measurement electrode replacement section 16.

Figure 24:
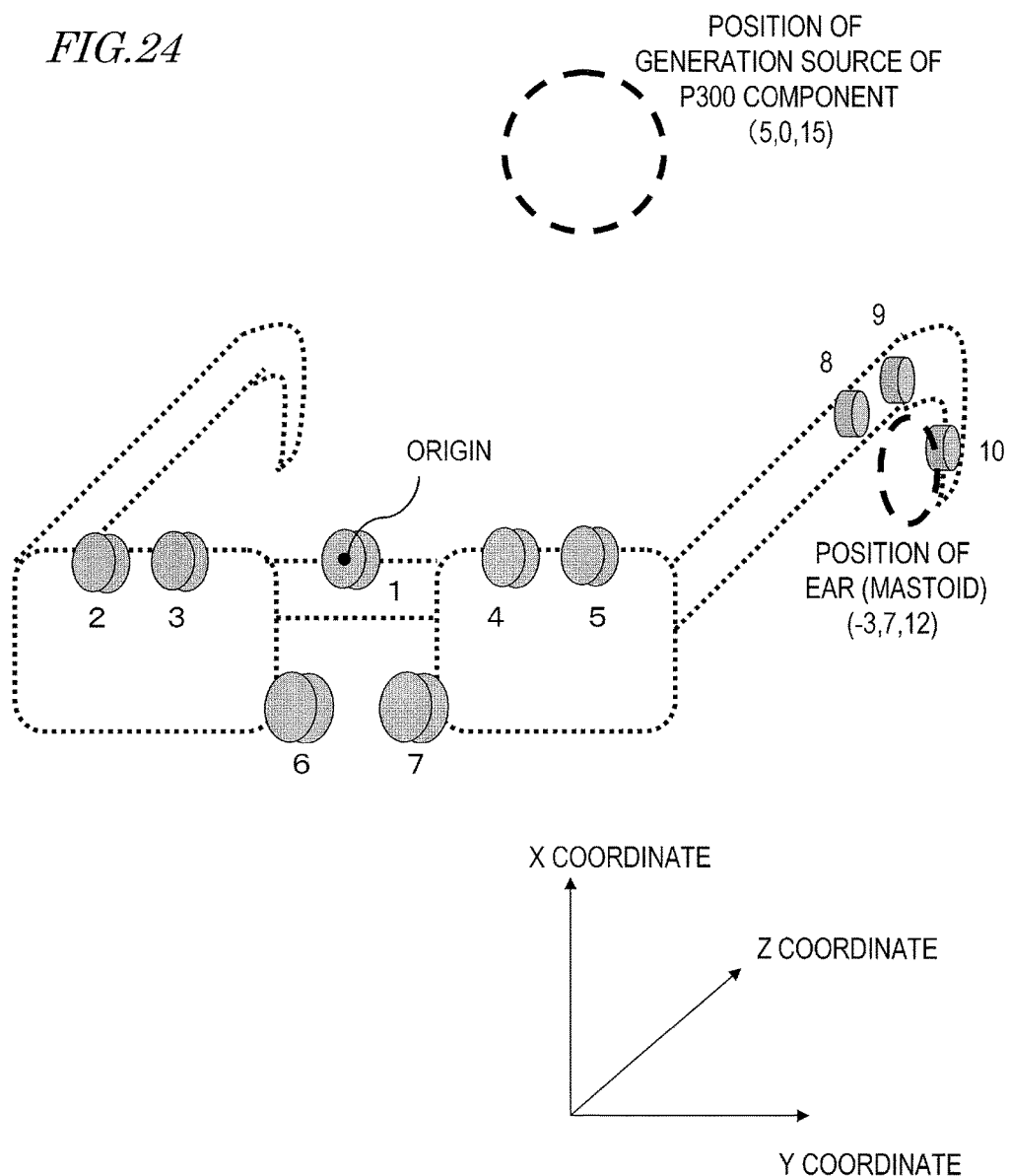

FIG. 24 is a diagram showing an example of electrode positioning in Embodiment 2.

FIG. 25 is a diagram showing an example of electrode information retained by the measurement electrode replacement section 16.

Figure 26:
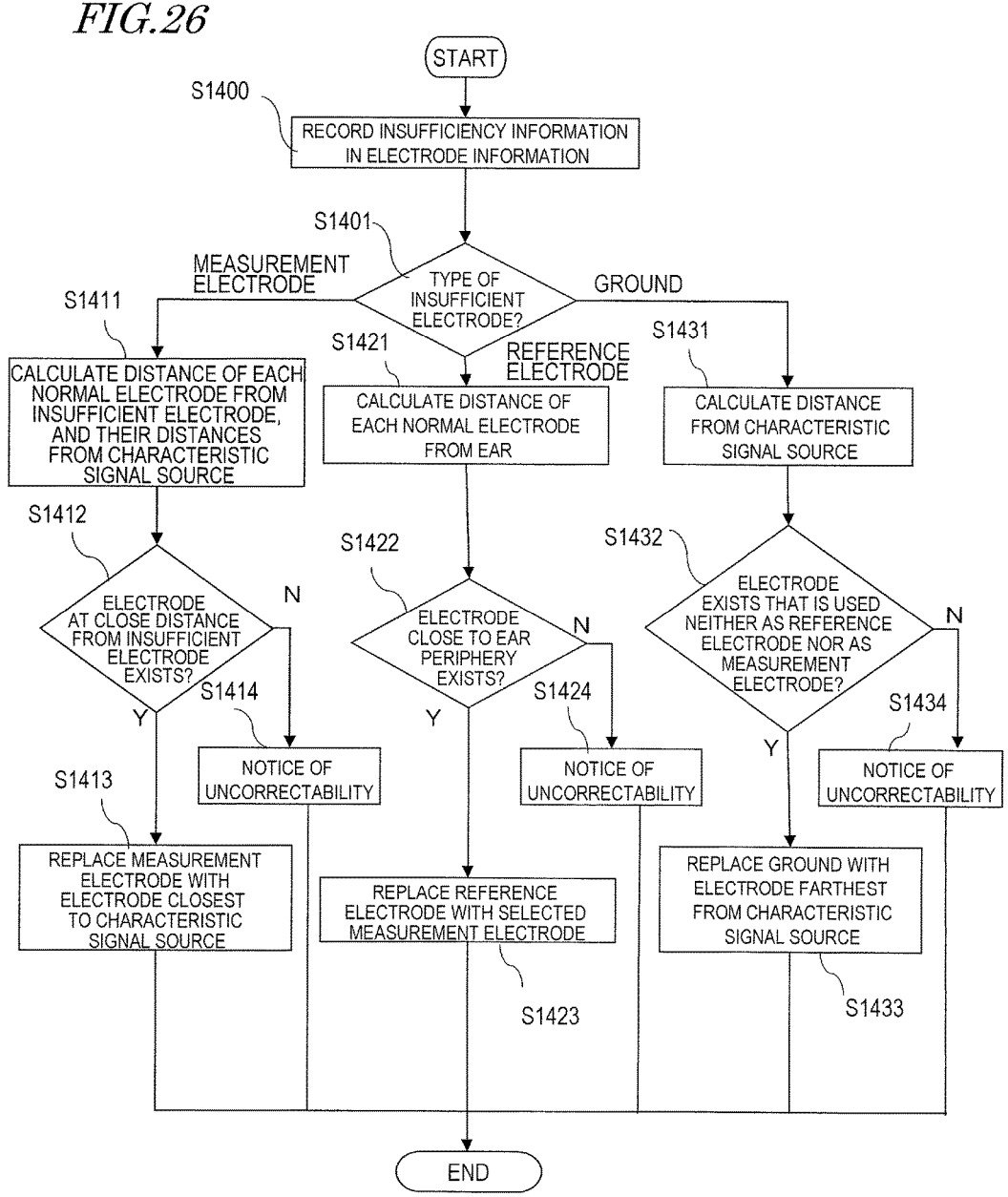

FIG. 26 is a flowchart showing a procedure of processing by the measurement electrode replacement section 16 performed at steps S1110, S1111, and S1112 in FIG. 23.

DETAILED DESCRIPTION OF PREFERRED EMBODIMENTS

First, principles of the present invention will be described, and thereafter embodiments of the present invention will be described.

In regard to cases where a plurality of types of electrodes ("measurement electrode", "reference electrode", and "ground") of an electroencephalograph respectively suffer from insufficiencies, the inventors have conducted an experiment to examine what sort of influence is exerted on the electroencephalogram waveform in each case. As a result of this, the inventors have found this characteristic feature: depending on what kind of and how much noise is mixed and the type of insufficiency, it is possible to identify a particular electrode type which has become insufficient, by merely relying on the electroencephalogram waveform.

As used herein, a "measurement electrode" is an electrode which is worn at a site where an encephalic activity to be measured is occurring. A "reference electrode" is an electrode which is worn at an ear periphery (earlobe or mastoid) or the like, where there is little influence of encephalic activities. "Ground" refers to an electrode which is worn for the purpose of removing in-phase noises through differential amplification.

Hereinafter, an exemplary construction of an electroencephalograph having the aforementioned electrodes ("measurement electrode", "reference electrode", and "ground") will be described. Thereafter, details of experiments performed by the inventors and novel findings obtained from the experimental results will be described, followed by a description of embodiments of insufficient electrode identification utilizing such findings.

Figure 1:
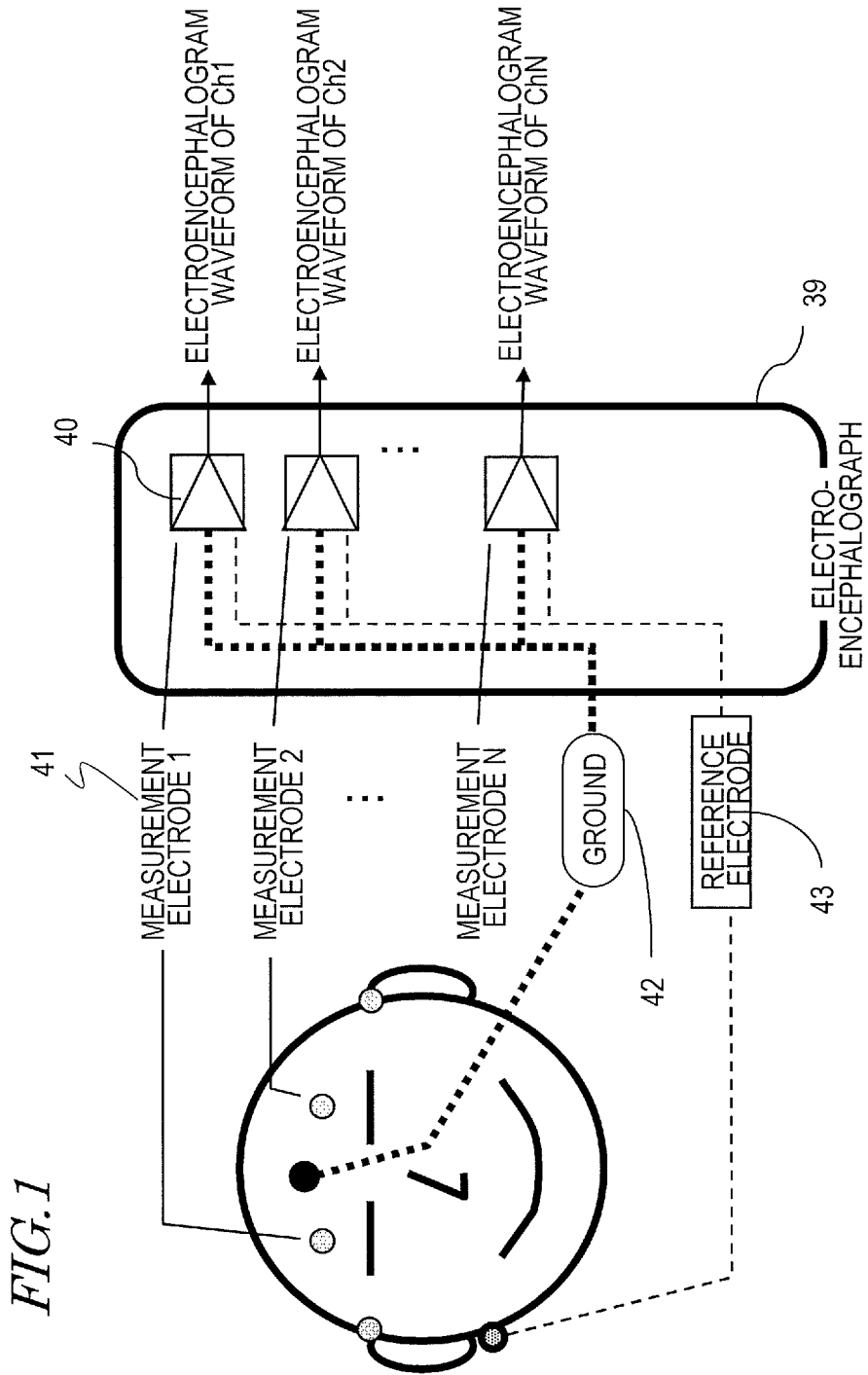
FIG. 1 is a diagram showing the construction of an electrode electroencephalograph 39 having a plurality of types of electrodes 41 to 43.

FIG. 1 shows the construction of an electrode electroencephalograph 39 having a plurality of types of electrodes 41 to 43. With reference to this figure, the relationship between the electrode type and an electroencephalogram signal (electroencephalogram channel) to be measured based on a potential difference between 1 set of electrodes will be described.

An electroencephalogram is measured in terms of potential difference between two electrodes which are worn on the head of a test subject. This potential difference corresponds to a potential change that has occurred in the brain of the test subject due to a neural activity. What defines an electroencephalogram waveform is representation of potential differences measured over a predetermined period.

The electroencephalograph 39 includes N measurement electrodes 41, a ground 42, and a reference electrode 43. Moreover, the electroencephalograph 39 includes differential amplifiers 40 corresponding to the N measurement electrodes 41.

Generally speaking, the measurement electrodes 41 (also referred to as "recording electrodes") are placed in sites at which encephalic activities for measurement are occurring. Moreover, the reference electrode 43 is placed at an ear periphery (earlobe or mastoid) or the like, where there is little influence of encephalic activities. Each differential amplifier 40 subjects a potential difference between a potential acquired by the reference electrode 43 and a potential acquired by the measurement electrode 41 corresponding to that differential amplifier 40 to differential amplification, and outputs the result. This output is the electroencephalogram signal at this site for measurement. The reason for providing the differential amplifier 40 is that a potential occurring in one's body is very weak and therefore needs amplification, and, when amplifying an electroencephalogram, it is necessary to remove in-phase components of external origin, e.g., AC noise generated by a commercial device.

When amplifying a potential difference between two electrodes (the measurement electrode 41 and the reference electrode 43) for measurement, in addition to the two electrodes, the differential amplifier 40 separately requires a ground input 42. The differential amplifier amplifies a potential difference between the ground 42 and the measurement electrode 41 (i.e., the voltage of the measurement electrode 41) and a potential difference between the ground 42 and the reference electrode 43 (i.e., the voltage of the reference electrode 43). Furthermore, the differential amplifier takes a difference between the voltage of the measurement electrode 41 and the voltage of the reference electrode 43. As a result, any noise component that is contained alike at the measurement electrode 41 and at the reference electrode 43 can be removed. As described above, the potential difference between the amplified voltage of the measurement electrode 41 and the amplified voltage of the reference electrode 43 is measured as one electroencephalogram signal (or electroencephalogram data).

The method of measuring an amplified potential difference between two electrodes (the measurement electrode 41 and the reference electrode 43) may be based on another method. For example, a difference between a potential difference between the ground 42 and the measurement electrode 41 (i.e., the voltage of the measurement electrode 41) and a potential difference between the ground 42 and the reference electrode 43 (i.e., the voltage of the reference electrode 43) may be taken. Then this difference may be amplified and measured as one electroencephalogram signal. This single electroencephalogram signal (or electroencephalogram data) is referred to as an "electroencephalogram channel". Each differential amplifier 40 outputs one electroencephalogram channel.

As described above, since one electroencephalogram is measured from the three electrodes of the measurement electrode 41, the ground 42, and the reference electrode 43, if even one of the three electrodes becomes insufficient, then the waveform of the electroencephalogram channel cannot be measured normally.

In a daily-life environment, any of the "measurement electrode", "ground", and "reference electrode" is liable to insufficient wearing. Hereinafter, manners in which insufficient wearing may occur will be described. As has been described in the section given to the problems of conventional techniques, insufficient wearing may occur not only in electrodes utilizing paste but also in dry electrodes. Hereinafter, dry electrodes will be taken as an example.

For example, FIGS. 2(a) to (e) show an example of an eyeglass-type head-mount display (HMD) 50 in which dry electrodes for electroencephalogram measurement are incorporated, and their states of attachment. In the example of FIG. 1, measurement electrodes 41 are disposed at two positions above the eyes; a ground 42 is worn at the nose; and a reference electrode 43 is disposed behind an ear.

In a normal state (a), where the HMD 50 is normally worn, the electrodes are properly in contact with the skin. If the user moves in daily life, e.g., into a bending-over posture, the HMD 50 will be shifted forward as shown in (b). At this time, the measurement electrodes 41 above the eyes and the nose ground 42 will be detached from the user's skin, thus resulting in an insufficient state of electrode attachment.

Moreover, if the HMD 50 has been worn for a long time, the mass of the HMD may cause the HMD 50 to be shifted in the lower direction, as shown in (c). At this time, the measurement electrodes 41 above the eyes will suffer from insufficient wearing. Moreover, when the HMD 50 is touched for manipulation or adjustment, after an intense motion has been made, and so on, a state where the HMD 50 is lopsided may occur as shown in (d). As a result, the measurement electrodes 41 above the eyes and the ear reference electrode 41 may be detached from the user's skin, thus resulting in insufficient wearing. Furthermore, when bumping into something, etc., a state where the HMD 50 is shifted sideways may occur as shown in (e). In this state, it is expected that any one of the measurement electrode 41 above one eye or the nose ground 42, and the ear reference electrode 43 may become disengaged. Thus, due to motion or position shifting of the HMD 50, not only the measurement electrodes 41, but also the ground and reference electrodes are also liable to insufficient wearing.

Therefore, the inventors have conducted an experiment as follows.

Contemplating a situation where an electroencephalograph is incorporated into the aforementioned head-mount display (HMD), the inventors disposed the electrodes of an electroencephalograph within the range of the shape of an HMD. In the present specification, the "range of the shape" of a wearable device such as an HMD refers to a range that is occupied by a shape which is usually required of that device. For example, FIGS. 3A and 3B show positioning of electrodes which are provided within the range of the shape of an hair band 25 of an HMD. The electrodes are provided within a range of the head of the test subject that is covered by the hair band 25 as indicated by a broken line. The range of the HMD shape is also inclusive of the range that is covered by the hair band 25.

Specific examples of measurement electrode positions are as follows. First, a reference electrode 22 is disposed behind the right ear; a measurement electrode 1 (a measurement electrode 23b in FIG. 3A) is disposed above the left eye; and a measurement electrode 2 (a measurement electrode 23a in FIG. 3A) is disposed above the right eye. Then, a ground 21 is disposed at a position shown in the figure (this position corresponding to the FPz position according to the position notation of the International 10-20 system).

The reference electrode 22 is disposed behind an ear, which is far in distance from the brain (i.e., the generation source of an electroencephalogram), whereas the measurement electrodes 23 are disposed in two places above both eyes, which are close to the brain. This makes it possible to measure two electroencephalogram channels. Specifically, channel 1 (Ch1) is obtained with a combination of the ground 21, the reference electrode 22, and the measurement electrode 1, whereas channel 2 (Ch2) is obtained with a combination of the ground 21, the reference electrode 22, and the measurement electrode 2. As described above, a "channel" is an electroencephalogram signal (or electroencephalogram data) which is measured by a single differential amplifier (i.e., one measurement electrode, the reference electrode, and the ground being combined).

All of the electrodes used in the experiment, i.e., the measurement electrodes, the reference electrode, and the ground, are dry electrodes to be worn without paste. Silver-silver chloride active electrodes (i.e., electrodes which allow amplification to be performed not only inside the electroencephalograph but also inside the electrodes) are used as the measurement electrodes and the reference electrode, and a silver-silver chloride disk electrode is used as the ground, these being fixed with the hair band 25. Polymate AP-1124 (manufactured by DIGITEX LAB. CO., LTD) was used for the electroencephalogram measurements. A measurement experiment was conducted for a test subject aged in the thirties, with a sampling frequency of 200 Hz and a time constant of 0.3 seconds.

The inventors have contemplated that the noise amount will fluctuate when any electrode becomes insufficient. Accordingly, changes in power at each frequency were observed, in a state where the electrodes were normally worn, and also in a state where an insufficiency in electrode attachment had occurred. Among others, attention was paid to the power of 60 Hz noise from commercial power, which is considered as the greatest external noise source, and to the power of the entire frequency band of the measured electroencephalogram, which is considered to reflect the entirety of the noise amount.

In electroencephalogram measurements, the amplitude voltage of an electroencephalogram signal to be measured is weak and in units of μV. On the other hand, the amplitude voltage of a noise component such as the 60 Hz noise from commercial power is in units of mV, which is greater than the amplitude voltage of an electroencephalogram signal. Moreover, a signal of brain origin is in the frequency band of 30 Hz or less. Thus, the 60 Hz noise from commercial power can be easily distinguished from a signal of brain origin. On the contrary, in electromyogram measurements, for example, the average potential of an electromyogram is generally said to be on the order of several μV to several mV, with frequency components from several Hz to several 100 Hz; therefore, a potential of electromyogram origin is difficult to be distinguished from the 60 Hz noise from commercial power.

Therefore, the inventors have analyzed two kinds of parameters, i.e., noise amount and total frequency power.

The experiment determined an "amount of mixed AC noise", as an example of the noise amount. An amount of mixed AC noise is meant as an amount of commercial-power noise of an external device. The amount of commercial-power noise of an external device is a frequency power of the external device in the frequency band of commercial power. As the frequency band of commercial power of an external device, a frequency depending on the country and locality, e.g., 50 Hz or 60 Hz, is selected.

As the total frequency power, "an average value of power in the analyzable frequency band" was determined. More specifically, 1 second of data was extracted from the measured electroencephalogram, and this was subjected to a fast Fourier transform (FFT) to determine a power value of each frequency; and a total frequency power was calculated as an average value of the power in a frequency band which is greater than 0 but equal to or less than 100 Hz. The reason for adopting "greater than 0 but equal to or less than 100 Hz" is that, given the fact that electroencephalogram measurements were taken with a sampling frequency of 200 Hz in this experiment, the sampling theorem dictates that the available frequency band is up to 100 Hz. The range of "greater than 0 but equal to or less than 100 Hz" is only exemplary. An available frequency band may be determined, and an electroencephalogram may be measured with a sampling frequency that is twice as large as the maximum frequency thereof.

In the present embodiment, the total frequency power is utilized as an index for checking for changes in the power of noises mixing in the available broad frequency band. The total frequency power is also utilized as an index for checking whether noises are mixed widely across a frequency band that is not associated with encephalic activities (i.e., a region of 30 Hz or above). Therefore, within the region of 30 Hz or above, by calculating a power average in a region accounting for a half or more of the available frequency band, a similar tendency to that of a power average value across the entire available frequency band (i.e., 0 to 100 Hz) will presumably be observed. Examples may be a range of 30 Hz or more but 100 Hz or less, or a range of greater than 0 Hz but 60 Hz or less.

FIG. 4 shows results of the electroencephalogram analysis. FIG. 4 shows amounts of mixed AC noise and total frequency powers in channels 1 and 2 (Ch1, Ch2) for each of five different states. The five different states are: "all electrodes are properly worn (normal)", "only measurement electrode 1 is shifted (shifting measurement electrode 1)", "only measurement electrode 2 is shifted (shifting measurement electrode 2)", "the reference electrode is shifted (shifting reference electrode)", and "the ground is disengaged (disengaging the ground)". As used herein, "shifting" refers to a state where an electrode is moved to the right or left while the electrode remains attached on the skin.

From the values shown in a framing 501 in the rightmost column of FIG. 4, it can be seen that the amount of mixed AC noise increases only when the ground becomes insufficient (disengaging the ground), and that not much increase is seen in a normal state or when any other electrode becomes insufficient. On the other hand, when a measurement electrode becomes insufficient (shifting measurement electrode 1 or shifting measurement electrode 2), the total frequency power increases only in the channel that corresponds to the insufficient measurement electrode, as is indicated by the values in a framing 502 across two places in FIG. 4. From the values in a framing 503 in FIG. 4, it can be seen that both channel 1 and channel 2 increase when the reference electrode becomes insufficient (shifting reference electrode).

These experimental results have led to the finding that: the amount of mixed AC noise increases when the ground becomes insufficient; the total frequency power of a channel corresponding to the measurement electrode increases when a measurement electrode becomes insufficient; and the frequency powers of all channels increase when the reference electrode becomes insufficient.

Furthermore, in order to confirm whether the above finding dictates a phenomenon that occurs similarly in any other test subject, the inventors have conducted an electroencephalogram measurement experiment in 14 test subjects in their twenties. Given the same electroencephalograph, electrodes, and electrode positions as above, the experiment was conducted to measure amounts of mixed AC noise and total frequency powers in three states: (a) a state where all electrodes are correctly worn; (b) a state where the ground is insufficient (e.g., the ground is disengaged); and (c) a state where a measurement electrode is insufficient (e.g., the measurement electrode 1 is disengaged).

FIG. 5 shows an average value of amounts of mixed AC noise of all test subjects and an extent of variations among all test subjects in the three states of (a) normal, (b) disengaging the ground, and (c) disengaging a measurement electrode. Similarly to the results 501 in FIG. 4, in all test subjects, FIG. 5 indicates a tendency that the amount of mixed AC noise increases when (b) disengaging the ground, as compared to any other state.

FIG. 6 shows an average value of total frequency powers of all test subjects and an extent of variations among all test subjects in the three states of (a), (b), and (c) above. As shown in FIG. 6, similarly to the results in the framing 502 of FIG. 4, (c) a tendency found among all test subjects was that the total frequency power increases when a measurement electrode is disengaged, as compared to any other state.

This experiment was not directed to reference electrode insufficiencies. However, from the increased total frequency power associated with measurement electrode insufficiencies as indicated by the results of FIG. 6, it is presumable that the total frequency powers of all channels will increase also when the reference electrode becomes insufficient, similarly to the results in the framing 503 of FIG. 4.

It was learned from the above results that the above finding (i.e., the amount of mixed AC noise increases when the ground becomes insufficient; the total frequency power of a channel corresponding to the measurement electrode increases when a measurement electrode becomes insufficient; and the frequency powers of all channels increase when the reference electrode becomes insufficient) is not any specific tendency that is test-subject dependent.

The above finding has led to the concept that a ground insufficiency can be determined based on an increase in the amount of mixed AC noise, that a measurement electrode insufficiency can be determined based on an increase in the total frequency power in a specific channel, and that a reference electrode insufficiency can be determined based on an increase in the total frequency power of every channel.

Hereinafter, embodiments of an electrode attachment state determination system according to the present invention, which are made based on this concept, will be described with reference to the drawings.

As preferable embodiments of the present invention, the inventors will illustrate an electroencephalogram interface system having an electrode attachment state determination function (hereinafter referred to as an "electrode attachment state determination system") for measuring an electroencephalogram of a user, determining a state or intent of the user based on a characteristic signal in the measured electroencephalogram, and feeding back the result of determination.

In particular, the electrode attachment state determination system measures an electroencephalogram with dry electrodes (not utilizing paste) being incorporated in a wearable device such as an HMD. Dry electrodes are particularly susceptible to insufficiencies in the state of electrode attachment. When such an insufficiency concerning the state of electrode attachment occurs, a notice or restoration determination is made for the user. When possible, measurements can be continued with replacement of electrodes.

(Embodiment 1)

FIG. 7 shows the functional block construction of an electrode attachment state determination system 20 according to the present embodiment. FIG. 8 shows an exemplary shape of a device which embodies the electrode attachment state determination system 20 in the form of an HMD. FIG. 9 shows an exemplary hardware construction of the electrode attachment state determination system 20. Among the constituent elements shown in each figure, like constituent elements are denoted by like reference numerals.

In the present specification, the electrode attachment state determination system 20 will be described on the basis of an HMD shape shown in FIG. 8. The respective portions of the HMD are expressed by using terms that indicate eyeglass portions. FIG. 10 shows the names of respective portions of eyeglasses. Portions which hang on the ears of a user 10 to fix the HMD main body will be referred to as "endpiece portions". Portions which come in contact with the nose of the user 10 to support the HMD main body will be referred to as "nose pad portions". A portion which supports and fixes an output section 13 that is disposed before either eyeball of the user 10 will be referred to as a "rim portion". A portion connecting and supporting the rim portion 23 in front of both eyes will be referred to as a "bridge portion". A portion connecting and support each rim portion and each endpiece portion will be referred to as a "temple portion".

As shown in FIG. 7, the electrode attachment state determination system 20 includes an electroencephalogram measurement/processing section 18 and an electrode state determination processing section 19. FIG. 7 illustrates the user 10 for ease of understanding.

The electroencephalogram measurement/processing section 18 includes an electroencephalogram measurement section 11, an electroencephalogram processing section 12, and an output section 13. The electrode state determination processing section 19 includes a frequency analysis section 14 and an insufficient electrode determination section 15. Hereinafter, the respective constituent elements will be described.

The electroencephalogram measurement section 11 of the electroencephalogram measurement/processing section 18 includes a ground 21, a reference electrode 22, measurement electrodes 23a and 23b, and an electroencephalogram measurement circuit 24 shown in FIG. 8. The ground 21 is disposed on a nose pad portion of the eyeglasses; the reference electrode 22 is disposed inside an endpiece portion of the eyeglasses; the measurement electrode 23a and measurement electrode 23b are disposed above the lenses of the eyeglasses; and the electroencephalogram measurement circuit 24 is disposed on a temple portion of the eyeglasses. The electrodes 21, 22, 23a, and 23b are disposed so that they come into contact with the skin of the user 10 when the HMD is worn.

From the measured electroencephalogram signal, the electroencephalogram processing section 12 distinguishes the intent or state of the user 10.

The output section 13 is a device (e.g., a liquid crystal monitor) which is disposed on a lens portion of the HMD for feeding back the result of distinction to the user 10. The feedback is realized as a device operation, e.g., an image output being made to the liquid crystal monitor.

On the other hand, the frequency analysis section 14 of the electrode state determination processing section 19 is disposed on the bridge portion of the HMD for subjecting the electroencephalogram measured by the electroencephalogram measurement section 11 to frequency analysis.

From the value of frequency analysis, the insufficient electrode determination section 15 determines an electrode which has become insufficient, and notifies the electrode state to the user 10 via the output section 13.

The functional blocks and electrode positions in FIG. 8 are exemplary, and the positions of the functional blocks, the positions of the electrodes, and the number thereof are not limited thereto.

Next, the hardware construction of the electrode attachment state determination system 20 will be described with reference to FIG. 9.

The ground 21, the reference electrode 22, the plurality of measurement electrodes 23, and the electroencephalogram measurement circuit 24 constitute the electroencephalogram measurement section 11 according to the present embodiment. The ground 21, the reference electrode 22, and the plurality of measurement electrodes 23 are connected to the electroencephalogram measurement circuit 24. The electroencephalogram measurement circuit 24 is connected to a bus 100 for exchange of electroencephalogram signals with other constituent elements.

A CPU 121, a RAM 122, and a ROM 123 constitute the electroencephalogram processing section 12 according to the present embodiment. The CPU 121 reads a computer program 124 which is stored in the ROM 123 onto the RAM 122, where the computer program 124 is laid out and executed. Based on the computer program 124, the electroencephalogram processing section 12 of the present embodiment realizes electroencephalogram distinction processing. The CPU 121, the RAM 122, and the ROM 123 are connected to the bus 100 for exchange of control signals and data with the respective constituent elements.

A CPU 141, a RAM 142, and a ROM 143 constitute the frequency analysis section 14 according to the present embodiment. The CPU 141 reads a computer program 144 which is stored in the ROM 143 onto the RAM 142, where the computer program 144 is laid out and executed. Based on the computer program 144, the frequency analysis section 14 of the present embodiment realizes a frequency analysis process for the electroencephalogram waveform. The CPU 141, the RAM 142, and the ROM 143 are connected to the bus 100, and send data representing the analysis result to the insufficient electrode determination section 15.

A CPU 151, a RAM 152, and a ROM 153 constitute the insufficient electrode determination section 15 according to the present embodiment. The CPU 151 reads a computer program 154 which is stored in the ROM 153 onto the RAM 152, where the computer program 154 is laid out and executed. Based on the computer program 154, the insufficient electrode determination section 15 of the present embodiment realizes an insufficient electrode determination process described below. The CPU 151, the RAM 152, and the ROM 153 are connected to the bus 100 for exchange of control signals and data with the output section 13.

The output section 13 includes an image processing circuit 131 and a screen 132. In accordance with control signals and data from the CPUs 121 and 141, the image processing circuit 131 outputs a feed back to the user 10 (e.g., an electroencephalogram waveform being displayed on the screen) and information of the state of electrode attachment on the screen 132. The output section 13 may also have a function of presenting necessary information on the HMD.

Each of the aforementioned computer programs 124, 144, and 154 may be distributed on the market in the form of a product recorded on a semiconductor memory medium or a storage medium such as a CD-ROM, or transmitted through telecommunication lines such as the Internet.

Note that the electroencephalogram processing section 12, the frequency analysis section 14, and the insufficient electrode determination section 15 may each be implemented as a piece of hardware (e.g., a DSP) consisting of semiconductor circuitry having the computer program(s) incorporated therein, or as a semiconductor device which performs calculations by its own circuitry, not via a CPU. Although the electroencephalogram processing section 12, the frequency analysis section 14, and the insufficient electrode determination section 15 are illustrated as functional blocks having separate CPUs, RAMs, and ROMs, their functions may similarly be realized by a shared CPU, RAM, and ROM.

Next, an outline of the electrode attachment state determination system 20 of the present invention will be described, and after briefly discussing the processing thereof, a method of determining insufficiencies concerning the state of electrode attachment will be described.

The electrode attachment state determination system analyzes the measured electroencephalogram, and when any insufficiency in the state of electrode attachment has occurred, identifies the insufficient electrode and notifies it to the user. When there is no insufficiency, no notice concerning the state of attachment is provided to the user, but the routine functions of electroencephalogram measurement and electroencephalogram analysis are provided. The functions provided through electroencephalogram analysis may be determination of a user state and extraction of an intent of device manipulation, for example.

The electroencephalogram processing in the present embodiment will be illustrated by taking as an example an electroencephalogram interface which determines a user's intent of selection by utilizing his or her electroencephalogram. More specifically, an electroencephalogram interface will be described which manipulates a TV set by utilizing an electroencephalogram signal from the user 10, and selects a program of a genre which the user 10 wishes to view.

FIG. 11(a) shows an exemplary screen of the electroencephalogram interface. More specifically, FIG. 11(a) shows an example of a menu which the output section 13 presents to the user 10 via a screen 41 of the TV set. On the screen, a question 42 "Which program do you want to watch?" and options 43a to 43d that are candidates of a program whose watching may be desired are presented. Herein four options ("baseball" 43a, "weather forecast" 43b, "cartoon show" 43c, and "news" 43d) are being displayed.

In the example of FIG. 11(a), the topmost "baseball" 43a is being selected for highlight indication. "Highlight indication" means an indication against a brighter background or in a bright text color than other item, or an indication pointed to by a cursor or the like. Herein, it suffices if it is clear which item the system currently wants attention to, when looked at by the user 10. After the fourth "news" 43d, it returns to the topmost "baseball" 43a.

FIG. 11(b) shows an event-related potential of an electroencephalogram signal of the user 10 which is acquired by the electroencephalogram processing section 12. The starting point of event-related potential acquisition is set to a moment at which each option is highlighted. Then, an event-related potential from e.g. 200 ms before to 1 second after this moment is extracted from the electroencephalogram signal. As a result, the response of the user 10 to the highlighted item is obtained. An event-related potential 44d is shown, where the horizontal axis represents time and the vertical axis represents event-related potential. The upper direction on the vertical axis corresponds to a direction in which the event-related potential becomes minus (negative), whereas the lower direction corresponds to a direction in which the event-related potential becomes plus (positive).

It is now assumed that the user 10 wishes to watch the weather forecast 43b. Among electroencephalogram signals 44a to 44d respectively corresponding to the options 43a to 43d, the electroencephalogram signal 44b of the user 10 when the weather forecast 43b is highlighted indicates that a characteristic positive component (P300 component) appears at a latency of about 300 ms from the starting point, i.e., a point in time of highlighting the weather forecast 43b. Therefore, on the premise that the option for which this P300 component was detected is the program which the user 10 wishes to view, the electroencephalogram processing section 12 switches the channel to the weather forecast channel. FIG. 11(c) shows a screen 45 after the weather forecast channel has been selected.

FIG. 12 shows a procedure of electroencephalogram interface processing by the electroencephalogram processing section 12.

At step S1501, the electroencephalogram processing section 12 displays a menu 23 shown in FIG. 11(a) via the output section 13. At step S1502, the electroencephalogram processing section 12 selects baseball 43a among the items, and at the next step S1503, displays the selected item, i.e., baseball 43a, with highlighting via the output section 13.

At step S1504, from the electroencephalogram signal which is output from the electroencephalogram measurement section 11, the electroencephalogram processing section 12 acquires an event-related potential based on the timing of highlighting the item as a starting point.

At step S1505, the electroencephalogram processing section 12 determines whether any waveform change that is associated with the highlighting of the item to be selected exists or not in the acquired event-related potential. If such a waveform change exists, control proceeds to step S1506; if no such waveform change exists, control returns to step S1502 to highlight a next item (e.g., weather forecast 43b). By identifying the presence or absence of a P300 component, it becomes possible to determine whether the currently acquired electroencephalogram waveform is a waveform for the item which the user 10 wishes to select or a waveform for an item which the user 10 does not wish to select.

Finally, at step S1506, the electroencephalogram processing section 12 executes a function corresponding to the item for which the P300 component has appeared (i.e., channel switching).

Through the above processes, the user 10 is able to select a menu item based on his or her electroencephalogram, without manipulating any buttons. Although it is illustrated that items are to be sequentially selected at step S1502, a method of random presentation would also be possible. This may enable a more careful menu selection because it is unknown which item will be selected next.

FIG. 13 shows a flowchart of an overall processing by the electrode attachment state determination system 20. Hereinafter, an operation will be described in accordance with the flowchart of the electrode attachment state determination system 20 in FIG. 13.

At step S1101, the electroencephalogram measurement section 11 measures an electroencephalogram of the user 10. The electroencephalogram measurement is taken by the electroencephalogram measurement circuit 24 with respect to each set (channel), where one set is defined by three types of electrodes shown in FIG. 8, i.e., the ground 21, the reference electrode 22, and a measurement electrode 23 corresponding to the measurement channel. Note that the ground 21 and the reference electrode 22 are commonly shared among the respective sets.

On the basis of the potential of the ground 21, the electroencephalogram measurement circuit 24 performs a differential amplification. Specifically, the electroencephalogram measurement circuit 24 amplifies the potential of the reference electrode 22 and the potential of the measurement electrode 23 on the basis of the potential of the ground 21, and takes a difference of the amplified potential of the reference electrode 22 from the amplified potential of the measurement electrode 23. As a result, an electroencephalogram potential of the measurement electrode 23 based on the reference electrode 22 can be measured. This differential amplification is to be used for amplifying weak signals, and also used in electroencephalogram measurements. The electroencephalogram potential measured in the above manner is sent to the electroencephalogram processing section 12 and to the frequency analysis section 14 as one channel of electroencephalogram data.

At step S1102, the frequency analysis section 14 performs a frequency analysis process. FIG. 14 shows an example of an electroencephalogram signal waveform to be processed by the frequency analysis section 14. The frequency analysis section 14 receives an electroencephalogram signal 301 which has been measured by the electroencephalogram measurement section 11, and extracts an electroencephalogram waveform 302 from a zone for determination. The zone to be extracted here is prescribed to be 1 second, for example. Next, the frequency analysis section 14 subjects the extracted electroencephalogram signal 302 to a frequency analysis based on fast Fourier transform (FFT), for example, and calculates power values 303 of respective frequencies. The power values 303 of respective frequencies correspond to Fourier coefficient values that are obtained from the fast Fourier transform (FFT).

After the power value calculation, the frequency analysis section 14 outputs the result of frequency analysis to the insufficient electrode determination section 15. After outputting the frequency analysis result, the frequency analysis section 14 waits until 1 second of electroencephalogram is measured, and after the lapse of 1 second, again executes a frequency analysis. If no process timing for the frequency analysis section 14 arrives during the zone for analysis or longer, the electroencephalogram data from 1 second immediately before the process timing is subjected to a frequency analysis.

At step S1103 in FIG. 13, the insufficient electrode determination section 15 determines whether each of the electrodes used for electroencephalogram measurement is suffering from insufficient wearing or not. From the frequency analysis result from the frequency analysis section 14, the insufficient electrode determination section 15 extracts analysis parameters which are necessary for determining the state of electrode attachment, i.e., noise amount and total frequency power. Then, through a comparison between each analysis parameter and a predetermined threshold value, the insufficient electrode determination section 15 determines whether each of the ground, reference electrode, and measurement electrodes is suffering from insufficiency in the state of electrode attachment. If any such insufficiency has occurred, the insufficient electrode determination section 15 performs a process of identifying which of the ground, reference electrode, and measurement electrodes has become insufficient. The specific determination method will be described in detail later.

When an insufficient electrode is identified, at step S1106, the output section 13 notifies the position and type of the electrode which has become insufficient to the user 10.

If step S1103 determines that there is no insufficient electrode, the process proceeds to step S1104. At step S1104, the electroencephalogram processing section 12 performs a process utilizing the measured electroencephalogram. In the present embodiment, the electroencephalogram processing section 12 cuts out an electroencephalogram based on the timing of highlighting an option as a starting point, and determines whether a P300 component has appeared or not, thereby distinguishing which option the user 10 has intended to select.

At step S1105, the output section 13 displays the result of processing by the electroencephalogram processing section 12 on the screen or the like, thereby providing a feedback to the user 10. In the present embodiment, the output section 13 feeds back the option 137 selected by the user 10 on the screen 132, as shown in FIG. 11(b).

Through such processing, at the same time of presenting a result of electroencephalogram measurement to the user, if there is any insufficiency in the electrode attachment, the type and position of the insufficient electrode can be identified and notified to the user.

Next, the process of determining an insufficient electrode which is performed by the insufficient electrode determination section 15 at step S1103 will be described.

FIG. 15 shows a flowchart of processing by the insufficient electrode determination section 15 which is performed at step S1103 (FIG. 13). Hereinafter, the details of the process performed at step S1103 will be described.

At step S1201, the insufficient electrode determination section 15 acquires a frequency analysis result which is output from the frequency analysis section 14. As used herein, the frequency analysis result may be data of the frequency power value of each frequency band. For example, in the case of recording the electroencephalogram with a sampling period of 200 Hz, it will be a result of a frequency analysis (FFT) with half a period thereof, i.e., from 0 to 100 Hz.

At step S1202, from the frequency analysis result of each electroencephalogram channel (Ch), the insufficient electrode determination section 15 calculates a characteristic noise frequency power. As used herein, a characteristic noise frequency is a frequency of noises occurring from an external device or the like in an environment in which the electroencephalogram is being measured. These noises are contained in the electroencephalogram signal at this frequency. For example, in an environment which is surrounded by electric devices, AC noise from the power source may be a characteristic noise. Inside an automobile or the like, a similar characteristic noise may be the pulse waves generated from the engine. The frequency of pulse waves generated from the engine will be in proportion to the engine revolutions. Therefore, by acquiring information representing the engine revolutions from a tachometer, a computer, or the like of the automobile, the insufficient electrode determination section 15 will be able to identify the frequency of the pulse waves.

By defining the aforementioned AC noise frequency or engine pulse wave noise frequency as a characteristic noise frequency, the characteristic noise frequency is calculated from the frequency analysis result of each channel. The present embodiment contemplates indoor use, and assumes that the characteristic noise is an AC noise. The AC noise band is 60 Hz in the kansai (west) region, and 50 Hz in the kanto (east) region, of Japan. Since the environment where the aforementioned experiment was conducted was in the kansai region, it is assumed that the characteristic noise frequency is 60 Hz, and the characteristic noise frequency power will read as the "amount of mixed AC noise" in the following description. Note that, the AC noise bands in other countries are 60 Hz for the United States of America, and 50 Hz for European countries and China. Based on the 60 Hz scenario described below, those skilled in the art should be able to conduct an experiment in any 50 Hz locality by considering the frequency difference.

At step S1203, from the frequency analysis result of each electroencephalogram channel, the insufficient electrode determination section 15 calculates a total frequency power. The total frequency power is calculated as an average value of the powers of the frequency analysis results (i.e., an average of frequency powers from 0 to 100 Hz).

In the processes of step S1204 and after, based on the values of the noise amount and total frequency power, the insufficient electrode determination section 15 determines which of the ground 21, the reference electrode 22, and the measurement electrode 23 has become insufficient. The flow of determination is in the following order: insufficiency determination for the ground 21 (step S1204), insufficiency determination for the measurement electrode 23 (steps S1205, S1206, and S1208), and then insufficiency determination for the reference electrode 22 (step S1209). These determination methods will be specifically described below.

First, the insufficient grounding determination performed by the insufficient electrode determination section 15 (step S1204) will be described. By referring to the amount of mixed AC noise calculated at step S1202, the insufficient electrode determination section 15 determines whether the ground 21 has become insufficient or not.

FIG. 16 presents, with respect to the results of the aforementioned experiment conducted by the inventors (FIG. 4) as an example, an exemplary graph representation of a frequency analysis result in the case where the ground 21 is normally worn (normal state) and a frequency analysis result in the case where the ground is disengaged (insufficient grounding). In the graph, the horizontal axis represents frequency (unit: Hz), and the vertical axis represents frequency power (unit: $\mu V^2$). This is a graph representation of frequency powers at 60 Hz in a normal state and under insufficient grounding, obtained by utilizing the amount of mixed AC noise of Ch1 in FIG. 4. According to FIG. 16, as compared to 82.3 $\mu V^2$ in the normal state, the value under insufficient grounding is 35502.3 $\mu V^2$, which is very different.

Therefore, a threshold value for ground insufficiency determination is set in the insufficient electrode determination section 15 in advance, and when the amount of mixed AC noise exceeds the threshold value, the insufficient electrode determination section 15 determines that the ground 21 has become insufficient. As the "threshold value", it is desirable to set an intermediate value between the normal state and insufficient grounding. However, by taking into consideration the discrepancy between the value in the normal state and the value under insufficient grounding, in the present embodiment, a logarithm of the amount of mixed AC noise in the normal state and a logarithm of the amount of mixed AC noise under insufficient grounding were averaged, and a frequency power that corresponds to this average value, i.e., 1700 $\mu V^2$, was set.

Another method of threshold value setting may be a method of, based only on the value in the normal state, defining an abnormal state by a value which is 10 times as large as that in the normal state (insufficient grounding state), i.e., 823 $\mu V^2$, for example. Through a comparison with this threshold value, in the experimental example of FIG. 4, the normal state will be determined as "no insufficient grounding", and control proceeds to step S1205. Moreover, the state of "disengaging the ground" will be determined as "insufficient grounding", and control proceeds to step S1210 of outputting a notice of insufficiency to the output section 13.

FIG. 17A shows an example of a notice of insufficiency when an insufficient grounding determination is made. As shown in FIG. 17A, an alarm indicating that the ground is disengaged is displayed on a screen 132. Alternatively, as shown in FIG. 17B, and image and explanation may be displayed on a screen 132 which indicates an electrode position where abnormal wearing is occurring.

Referring back to FIG. 15, the insufficiency determination process for the measurement electrodes 23 performed by the insufficient electrode determination section 15 (steps S1205, S1206, and S1208) will be described.

At step S1205, by utilizing the characteristics of the aforementioned experiment conducted by the inventors, the insufficient electrode determination section 15 compares the value of the total frequency power of any one channel that has been measured, against the threshold value for determining electrode insufficiency. If the total frequency power of an electroencephalogram channel for determination exceeds the threshold value, the insufficient electrode determination section 15 determines that the measurement electrode of the determined channel number may have become insufficient, and records the channel number in an insufficiency list at step S1208. Table 1 shows an exemplary insufficiency list in which the channel numbers which have become insufficient are recorded.

TABLE 1

| insufficient channel number |
|---|
| Ch1 |
| Ch5 |
| Ch6 |
| ... |
| Chk |

According to the above experimental results, the threshold value was set to 36, which is an intermediate value between the greater of the total frequency power values in the normal state (i.e., 5.2) and the smallest of the total frequency power values which have increased with an electrode insufficiency (i.e., 67.1).

In the experimental example of FIG. 4, when measurement electrode 1 is shifted, Ch1 whose total frequency power exceeds 36, is detected to be insufficient, and added to the insufficiency list. Another method of threshold value setting may be setting a threshold value for each channel, and based only on the value in the normal state, defining an abnormal state (measurement electrode insufficiency state) by a value which is twice as large as that of the normal state (e.g., 10.4 $\mu V^2$ for Ch1 and 5.6 $\mu V^2$ for Ch2).

Regarding the frequency power values at the time of insufficiencies, the same values as those obtained through the above experimental analysis will not always occur at the time of electrode insufficiencies; rather, they will presumably vary depending on the degree and extent of electrode shifting and on the skin state. However, the tendency will remain that the total frequency power increases at the time of insufficiencies over that in the normal state. Therefore, by taking into consideration the fluctuations in the total frequency power values at the time of insufficiencies, the threshold value for distinction may be set lower than the aforementioned value (e.g., 20 $\mu V^2$).

At step S1206, the insufficient electrode determination section 15 determines whether any electroencephalogram channel exists that has not been subjected to the comparison process of step S1205. If there is any, control returns to step S1205, and the electroencephalogram channel is subjected to the comparison process of step S1205.

If the comparison process of step S1205 has been completed fro all electroencephalogram channels, the process proceeds to step S1207. At step S1207, the insufficient electrode determination section 15 confirms the contents of the insufficiency list, and confirms the channel numbers described in the insufficiency list. If the insufficiency list contains no description and is empty, the insufficient electrode determination section 15 determines that there are no insufficient electrodes, and makes a "no insufficient electrodes" determination at step S1213.

If the insufficiency list is not empty, then at step S1209, the insufficient electrode determination section determines whether all of the electroencephalogram channels that are currently under measurement are in the insufficiency list or not. If all of the channels are in the insufficiency list, it is considered that the reference electrode 22 has become insufficient. Therefore, the insufficient electrode determination section 15 determines at step S1211 that the reference electrode is insufficient.

If step S1209 finds that the insufficiency list does not match all of the channel numbers, it is presumable that an individual measurement electrode(s) has become insufficient. At step S1212, the insufficient electrode determination section 15 determines that the measurement electrode(s) corresponding to the Ch number(s) in the insufficiency list is insufficient.

Now, the flow of the determination process shown in FIG. 15 will be discussed with reference to the results shown in FIG. 4 of the normal state, measurement electrode 1 being insufficient, measurement electrode 2 being insufficient, and the reference electrode being insufficient.

In the normal state, the insufficient electrode determination section 15 will not add Ch1 and Ch2 to the insufficiency list through the processes of steps S1205 to S1207 in FIG. 15. The reason is that the total frequency powers of Ch1 and Ch2, i.e., 5.2 and 2.8, are both under the threshold value of 36. Then, the insufficient electrode determination section 15 will confirm at step S1207 that the insufficiency list is empty, thus making a "no insufficient electrodes" determination.

When measurement electrode 1 is shifted, the total frequency power of Ch1, i.e., 93.7, exceeds the threshold value of 36. Therefore, through the processes of step S1205 and step S1208 in FIG. 15, the insufficient electrode determination section 15 will add channel numbers including measurement electrode 1 to the insufficiency list. Since the insufficient electrode determination section 15 determines that only Ch1 is insufficient at step S1209, measurement electrode 1 is determined as an insufficient electrode.

When the reference electrode is shifted, the total frequency powers of Ch1 and Ch2, i.e., 357.6 and 194.6, are both below the threshold value of 36. Therefore, through the processes of step S1205 and step S1208 in FIG. 15, the insufficient electrode determination section 15 will add Ch1 and Ch2 to the insufficiency list. At step S1209, determining that all channels are suffering from insufficiencies, the insufficient electrode determination section 15 determines the reference electrode to be the insufficient electrode.

Although the above description refers to the notifying methods shown in FIG. 17A and FIG. 17B to illustrate exemplary outputs of the output section 13, the notifying method to the user is not limited to the above. It may be any notifying method which is able to notify to the user 10 that insufficiencies in electrode attachment have occurred, which allows the user 10 to know where the insufficient electrodes are, and which urges the user to improve the situation. For example, an audio-based notifying method would also be encompassed by the present invention.

Through the above processes, it is possible to identify whether an electrode which has become insufficient is a measurement electrode, the reference electrode, or the ground. Not only measurement channels that are defined by a plurality of electrodes are identifiable, but also the particular electrode(s) which has become insufficient can be identified, and notices of such insufficiencies can be given. As a result, the user is able to immediately improve the state of attachment of the electrodes, thus allowing electroencephalogram measurement to be continued even in a daily-life environment which is susceptible to insufficient wearing.

With the above construction, when insufficiencies in electroencephalogram measurement occur, the user 10 is able to know the type and position of the electrode(s) which is suffering from insufficient wearing, and is able to correct the state of electrode attachment by himself or herself.

However, if the user 10 corrects an insufficient electrode, there is a possibility that an electrode which lies near the insufficient electrode but was worn normally (i.e., not insufficient) may newly suffer from electrode shifting or the like. As a result, the electrode which was normally worn before may now be determined as an insufficient electrode. Thus, every time the user performs a correction, notices of insufficiency concerning other electrodes may be issued, thus making it difficult for the overall correction to be completed.

Therefore, until restoration of an insufficient electrode is completed, the insufficient electrode determination section 15 may halt the electrode insufficiency determination process so that any electrode insufficiency will not be detected. In this case, the insufficient electrode determination section 15 may determine restoration of the insufficient electrode, for example, or, a restoration determination section may be provided for determining restoration of the insufficient electrode. As a result, the burden on the user 10 when correcting insufficient electrodes can be reduced.

Now, a method of the aforementioned determination of insufficient electrode restoration will be described.

The inventors have conducted an experiment to look for characteristic features of the electroencephalogram that distinguish a state where an electrode insufficiency has not been eliminated from a state where the electrode has been restored. As a result, they have found that, by detecting a characteristic feature which appears when an insufficient electrode is restored, it is possible to perform an electrode restoration determination process.

Hereinafter, details of this experiment and the novel findings obtained from the experimental results will be described, followed by a description of the details of a restoration determination process for insufficient electrodes that utilizes the findings.

In this experiment, similarly to the previous experiment, electrodes were worn by a test subject aged in the thirties at positions shown in FIGS. 3A and 3B: a reference electrode 22 behind the right ear; a measurement electrode 23a above the right eye; a measurement electrode 23b above the left eye; and a ground 21 at FPz according to the position notation of the International 10-20 system. Silver-silver chloride active electrodes were used as the measurement electrodes and as the reference electrode, whereas a silver-silver chloride disk electrode was used as the ground, each without using paste; and these were fixed with a hair band 25. Polymate AP-1124 (manufactured by DIGITEX LAB, CO., LTD) was used as an electroencephalograph. The measurements were taken with a sampling frequency of 200 Hz and a time constant of 0.3 seconds.

The experiment was conducted under the assumption that the measurement electrodes or the ground may be an insufficient electrode(s). It was assumed that a characteristic feature similar to that associated with the measurement electrodes will also appear for the reference electrode.

The assumed insufficiency state was "electrode disengagement", and a comparison was made between an electroencephalogram waveform of the case where an electrode was left disengaged and an electroencephalogram waveform of the case where an electrode was once disengaged and then immediately corrected and restored to the normal state. Specifically, the experiment was conducted in four states: "(a) the measurement electrode 23b is left disengaged"; "(b) the measurement electrode 23b is temporarily disengaged and then restored to the correct state"; "(c) the ground 21 is left disengaged"; and "(d) the ground 21 is temporarily disengaged and then restored to the correct state". The inventors measures electroencephalograms in the respective states, and conducted a comparison in the electroencephalogram waveforms between (a) and (b), which involves comparison between the measurement electrodes 23, and a comparison in the amounts of mixed AC noise between (c) and (d), which involves comparison concerning the ground 21.

FIGS. 18(a) to (d) respectively show results of the experiment concerning the four states indicated in (a) to (d) above. In each graph, the horizontal axis represents time (unit: second). In (a) and (b), the vertical axis represents potential (unit: μV), and the potential of the electroencephalogram of Ch1 is indicated by a solid line. In (c) and (d), the vertical axis represents frequency power (unit: μV^2), and transitions in the amount of mixed AC noise are indicated by a dotted line.

A comparison between the states of (a) and (b) in FIG. 18 indicates that, in state (a) where the measurement electrode 23b is left disengaged, the potential reaches 3000 μV, but thereafter the waveform remains flat. On the other hand, in state (b) where the measurement electrode 23b is once disengaged and then immediately restored, the waveform temporarily becomes flat, but an electroencephalogram waveform appears about several seconds after the electrode restoration. As used herein, "immediately" means about 2 to 3 seconds, for example.

A comparison between the states of (c) and (d) in FIG. 18 indicates that: in state (c) where the ground 21 is left disengaged, the amount of mixed AC noise continues to take values above 10000 µV^2; however, in state (d) where the ground 21 is once disengaged and then immediately restored, the amount of mixed AC noise temporarily increases to 5000 µV^2 after the ground is disengaged, but the amount of mixed AC noise after restoration of the ground again returns to low values similar to those before the ground is disengaged.

The comparisons between (a) and (b) and between (c) and (d) have led to a finding concerning the measurement electrode that an electroencephalogram waveform appears immediately after electrode restoration following the insufficiency detection. Therefore, by detecting whether an electroencephalogram waveform appears (i.e., the average and/or variance of the electroencephalogram data becomes non-zero) or not after detection of an electrode insufficiency, it is possible to determine whether the measurement electrode has been restored or not. As for the reference electrode, too, it should be possible to determine whether the reference electrode has been restored or not by subjecting an electroencephalogram of the arbitrary electroencephalogram channel to a determination on a similar basis.

The above comparisons have also led to a finding concerning the ground that the amount of mixed AC noise increases in value after an insufficient grounding, but a restoration allows the amount of mixed AC noise to return to the value in the normal state. Therefore, after an insufficient grounding is detected, it is possible to determine whether the ground has been restored or not by detecting whether the once-increased amount of mixed AC noise has returned to its normal value.

Hereinafter, with reference to the drawings, an electrode restoration determination section 17 which is constructed based on this concept will be described.

FIG. 19 shows the functional block construction of an electrode attachment state determination system 20a according to a variant of the present embodiment. In the electrode attachment state determination system 20a, instead of the electrode state determination processing section 19 shown in FIG. 7, an electrode state determination processing section 19a is provided. The electrode restoration determination section 17 for determining electrode restoration is added to the electrode state determination processing section 19a. The electrode restoration determination section 17 determines whether an electrode which became insufficient has been restored to a state which again enables electroencephalogram measurement. For example, the electrode restoration determination section 17 is introduced by newly providing similar hardware to that of the insufficient electrode determination section 15 shown in FIG. 9, and is connected via the bus 100. Alternatively, the program 154 shown in FIG. 9 may be adapted so that the CPU 151, RAM 152, and ROM 153 function as the insufficient electrode determination section 15 at one point in time, and as the electrode restoration determination section 17 at another point in time. The latter example is realized by the program 154 containing not only the procedure of processing by the insufficient electrode determination section 15 but also the procedure of processing by the electrode restoration determination section 17, which is described below. Note that the information of an electrode state that has been determined through the processing by the insufficient electrode determination section 15 is passed onto the processing by the electrode restoration determination section 17, whereby the below-described processes are executed.

FIG. 20 is a flowchart showing a procedure of processing by the electrode attachment state determination system 20a, to which the processing by the electrode restoration determination section 17 is added. As the additional processing by the electrode restoration determination section 17, after the process of notifying electrode insufficiencies (step S1106), a process of determining whether a proper state of attachment has been restored from an insufficient wearing state (step S1107) is added.

Hereinafter, with reference to FIG. 21, the details of the electrode restoration determination process (step S1107 in FIG. 20) performed by the electrode restoration determination section 17 will be described.

In FIG. 21, when an electrode insufficiency is detected by the insufficient electrode determination section 15 (step S1106 in FIG. 20), at step S1301, the electrode restoration determination section 17 begins electroencephalogram measurement for determination of electrode restoration. The electroencephalogram measurement is performed by the electroencephalogram measurement section 11.

At step S1302, based on the type of the insufficient electrode determination section 15, the electrode restoration determination section 17 changes the process of restoration. In the case where the insufficient electrode is the reference electrode 22 or the measurement electrodes 23, a determination of electrode restoration is made based on steps S1303 and S1304. On the other hand, in the case where the insufficient electrode is the ground 21, a restoration determination is made through the processes of steps S1305 and S1306.

First, the restoration determination process for the reference electrode 22 and the measurement electrodes 23 will be described.

At step S1303, from the measured electroencephalogram, the electrode restoration determination section 17 extracts an electroencephalogram channel that includes the insufficient electrode. For example, Ch1 is extracted in the case of the measurement electrode 23b. In the case of the reference electrode, either Ch1 or Ch2 is extracted, since it is included in both Ch1 and Ch2. The electrode restoration determination section 17 calculates an average value and variance of the electroencephalogram signal during a certain period (e.g., 1 second). Note that, unless the state of electrode attachment has been restored, the signal to be processed herein does not qualify as an "electroencephalogram signal"; however, it will nonetheless be referred to as an "electroencephalogram signal" for convenience.

At step S1304, the electrode restoration determination section 17 determines whether the average value and variance calculated at step S1303 are both 0 or not. This is equivalent to determining whether the measured electroencephalogram is flat or not. If both of the average value and variance are 0, the electroencephalogram is flat, i.e., no electroencephalogram is being detected from that electrode, which means that the insufficiency(s) has not been eliminated yet.

Thus, when the electroencephalogram is flat, it can be said that the insufficient electrodes have not been eliminated, and therefore the electrode restoration determination section 17 returns the process to step S1301 to continue determination of electrode restoration until the insufficiencies are eliminated. When the electroencephalogram is no longer flat and an electroencephalogram begins to be measured, it can be said that the electrode insufficiencies have been eliminated, and therefore the electrode restoration determination section 17 instructs the output section 13 to notify the user 10 that the insufficiencies the measurement electrodes 23 and the reference electrode 22 have been eliminated. Thereafter, the process is ended.

Upon receiving an instruction from the electrode restoration determination section 17, the output section 13 notifies the user 10 that the electrode insufficiencies have been eliminated at step S1307. For example, elimination of the electrode insufficiencies is notified by removing the alarm indication shown in the example of FIG. 17A or 17B from the screen.

Note that the notifying method is not limited to the above, and any other notifying method may be adopted. For example, as shown in FIG. 17C, an LED lamp may be provided outside the screen, and elimination of insufficiencies in the state of attachment may be notified by utilizing the color of the LED lamp. For example, the LED lamp may be activated in green in the normal state, or in red when insufficiencies have occurred, and again in green when the insufficiencies have been eliminated. Alternatively, an audio saying "Restored" or the like may be generated and used for notification. Furthermore, any notifying method other than visual is also encompassed by the present invention, e.g., allowing an alarm sound that is output as a notice while there is any insufficiency to be stopped upon restoration from the insufficiency.

Next, the restoration determination process for the ground 21 will be described.

FIG. 21 is referred to again. At step S1305, with respect to each channel of the measured electroencephalogram, the electrode restoration determination sections 17 extracts an electroencephalogram over a certain period (e.g., 1 second) and calculates an amount of mixed AC noise.

At step S1306, the electrode restoration determination section 17 determines whether the calculated amounts of mixed AC noise in all channels exceed a threshold value or not. For example, the threshold value is set to 1700 $\mu V^2$, which was utilized by the insufficient electrode determination section 15 for determining an insufficiency of the ground 21. If the amounts of mixed AC noise in all channels exceed this threshold value, the electrode restoration determination section 17 determines that the insufficiency of the ground 21 has not been eliminated, and returns the process to step S1301 to continue determination of electrode restoration until the insufficient grounding is eliminated. If the increase in the amounts of mixed AC noise subsides so that the amounts become below the threshold value, the electrode restoration determination section 17 determines that the insufficiency of the ground 21 has been eliminated, and instructs the output section 13 to notify the user 10 that the insufficiency of the ground 21 has been eliminated, and the processing by the electrode restoration determination section 17 is ended. The notice of restoration of the ground via the output section 13 is made in a similar manner to the notice of restoration of the measurement electrode 23 or the reference electrode 22 at step S1307.

By detecting a characteristic feature matching each insufficient electrode, which appears when the insufficient electrode is restored, as in step S1304 or S1306 above, it becomes possible to perform an electrode restoration determination process.

Thus, due to the addition of the electrode restoration determination section 17, after an electrode insufficiency occurs, insufficiency determination is not performed until the insufficient electrode is restored. This makes it unnecessary for the user to perform excessive corrections of the state of electrode attachment, whereby the burden of the user is reduced.

(Embodiment 2)

With the construction of Embodiment 1, when the state of attachment of an electrode becomes insufficient, the user 10 is able to know the type of electrode which is insufficiently worn, thus realizing a determination of the state of electrode attachment.

However, in a daily-life environment, it is expected that there are frequent chances for electrodes to become insufficient under the influence of the motions of the user 10, etc. Therefore, every time the user 10 undergoes a motion, a notice of an insufficient electrode is given by the construction of Embodiment 1, thus making it necessary for the user 10 to correct the electrode state.

Thus, what is needed is a function of, after detecting an insufficient wearing of an electrode, automatically restoring from the electrode insufficiency state to enable continued electroencephalogram measurement. The automatic restoration from an electrode insufficiency state is made by replacing an electrode which has become insufficient with an electrode that is normally worn. Thus, an electrode attachment state determination system which is capable of automatic restoration is realized by: retaining a plurality of substitutable electrodes; when an insufficiency occurs, choosing the proper electrode so as not to deteriorate the processing accuracy; and replacing it with a normal electrode.

Therefore, the present embodiment illustrates an electrode attachment state determination system possessing a plurality of substitutable electrodes in advance, which not only detects insufficient wearing of an electrode, but also determines a possibility of automatic restoration to a normal state of electroencephalogram measurement, and when electrode replacement is possible, makes an automatic replacement in order to continue electroencephalogram measurement.

FIG. 22 shows the functional block construction of an electrode attachment state determination system 200 according to the present embodiment.

In the electrode attachment state determination system 200, instead of the electrode state determination processing section 19 shown in FIG. 7, an electrode state determination processing section 190 is provided. The processing by the electroencephalogram measurement section 11, the electroencephalogram processing section 12, the output section 13, the frequency analysis section 14, the insufficient electrode determination section 15 is identical in both systems of Embodiments 1 and 2. Those constituent elements having like functions are denoted with like reference numerals, and the descriptions thereof are omitted. Hereinafter, the electrode state determination processing section 190 will be described.

An measurement electrode replacement section 16 is provided in the electrode state determination processing section 190. When the presence of an insufficient electrode is detected, the measurement electrode replacement section 16 switches to an electroencephalogram signal measurement that employs an electrode which is free of insufficiency, instead of the insufficient electrode. More specifically, the measurement electrode replacement section 16 determines whether there is any electrode that is capable of detecting an electroencephalogram signal with close electroencephalographic characteristics or not, determines the possibility of automatic restoration, and selects a candidate electrode which can be used in the place of the insufficient electrode. In the present specification, this operation of switching from one electrode to another electrode for use is referred to as "electrode replacement".

The measurement electrode replacement section 16 is introduced by newly providing similar hardware to that of the insufficient electrode determination section 15 shown in FIG. 9, and is connected via the bus 100. Alternatively, the program 154 shown in FIG. 9 may be adapted so that the CPU 151, RAM 152, and ROM 153 function as the insufficient electrode determination section 15 at one point in time, and as the measurement electrode replacement section 16 at a point in time when an insufficient electrode is detected. The latter example is realized by the program 154 containing not only the procedure of processing by the insufficient electrode determination section 15 but also the procedure of processing by the measurement electrode replacement section 16, which is described below. Note that the information of an electrode state which is determined through the processing by the insufficient electrode determination section 15 is passed onto the processing by the measurement electrode replacement section 16, whereby the below-described processes are executed.

FIG. 23 is a flowchart showing a procedure of processing by the electrode attachment state determination system 200, to which the processing by the measurement electrode replacement section 16 is added.

As compared to the processing of Embodiment 1 illustrated in FIG. 13, steps S1110 to S1112 are added in the present embodiment. Step S1110 is a process of restorability determination which, after an electrode insufficiency is detected, determines whether electroencephalogram measurement can be continued or not by replacing the insufficient electrode with another electrode. Step S1111 is an electrode replacement process of performing an electrode replacement in the case where automatic restoration is possible, thus enabling continued electroencephalogram measurement. Step S1112 is a process of notifying inability of automatic restoration where, when automatic restoration is impossible, the user 10 is notified that automatic restoration cannot be made, and urged to correct the electrode.

In the present embodiment, more electrodes than those in Embodiment 1 are provided so that, when an electrode becomes insufficient, the insufficient electrode can be replaced with a normal electrode.

FIG. 24 shows an example of electrode positioning in the present embodiment. In the present embodiment, ten electrodes are provided, to which electrode numbers 1 to 10 are assigned for uniquely identifying the respective electrodes (for ease of understanding, the electrode numbers are indicated by the electrodes in FIG. 24). Among the electrodes thus provided, a reference electrode, a ground, and a plurality of measurement electrodes are designated.

The measurement electrode replacement section 16 stores information concerning the electrodes in advance.

FIG. 25 shows an example of electrode information retained by the measurement electrode replacement section 16. The electrode information describes: electrode numbers; usage types each indicating which electrode type among the measurement electrode, the ground, or the reference electrode each given electrode is being used as; information of coordinates indicating the absolute position of each electrode; and the state of attachment of each electrode. In the case of the HMD-type electrode attachment state determination system 20, for example, the coordinates represent a relative position from an origin which is the position of the bridge portion center of the eyeglasses. This relative position is identified on the coordinate axes shown in FIG. 24, for example. In FIG. 24, the X coordinate represents the up-down direction of the HMD, the Y coordinate the right-left direction, and the Z coordinate the depth direction.

Hereinafter, the processing by the measurement electrode replacement section 16 will be described in detail.

FIG. 26 shows a procedure of processing by the measurement electrode replacement section performed at steps S1110, S1111, and S1112 in FIG. 23.

At step S1400, by relying on the electrode number of an electrode which has become insufficient, the measurement electrode replacement section 16 may record a state in the electrode information having become "insufficient". In this example, the "state" column of electrode number 3 in FIG. 25 is recorded as "insufficient". Note that, the format of FIG. 25 is only exemplary. The content of recording may be arbitrary so long as the method is able to provide unique identification of normal or insufficient. A value corresponding to normal (e.g., "0") and a value corresponding to insufficiency (e.g., "1") may be recorded. Alternatively, the electrode information may describe the types and positions of only those electrodes which are not insufficient. With such electrode information, electrode replacement is possible as the type(s) and position(s) of the insufficient electrode(s) become identified.

The measurement electrode replacement section 16 performs a different electrode replacement process depending on the type of electrode that is determined as insufficient. In other words, depending on whether the electrode type is ground, reference electrode, or measurement electrode, different electrode replacement processes are executed.

At step S1401, the measurement electrode replacement section 16 determines the type of the electrode which has been determined by the insufficient electrode determination section 15 as insufficient. If the determined electrode type is measurement electrode, the process proceeds to step S1411, whereafter steps S1412, S1413, and S1414 are executed. If the determined electrode type is reference electrode, the process proceeds to step S1421, whereafter steps S1422, S1423, and S1424 are executed. If the determined electrode type is ground, the process proceeds to step S1431, whereafter steps S1432, S1433, and S1434 are executed.

Hereinafter, an electrode replacement process for the measurement electrodes 23 will be described first.

If a measurement electrode becomes insufficient, it is necessary to replace it with an electrode which is capable of measuring an electroencephalogram signal which has similar characteristics to those of the electroencephalogram signal that has been measured with that measurement electrode. The reason is that, when performing electroencephalogram signal processing, the characteristic component of the electroencephalogram signal for processing needs to appear in similar manners before and after the measurement electrode replacement.

In order to allow the characteristic component of the electroencephalogram signal to appear in similar manners, it is necessary that the position of the replacing electrode is close to the position of the replaced electrode. Therefore, in order to continue electroencephalogram measurement with the characteristic component of the electroencephalogram signal being similarly detected, it is necessary to replace the measurement electrode that has become insufficient with an electrode which is at a close distance from that measurement electrode.

Moreover, disposing the electrode at a position close to a position in the brain that generates the characteristic component of the electroencephalogram signal will increase the intensity of the characteristic component, thus enabling electroencephalogram processing with a higher accuracy. Therefore, the requirements for the measurement electrode to be substituted (hereinafter referred to as the "replacing electrode") for the insufficient electrode are that its position is at a close distance from the insufficient electrode and at a close distance from the generation source of the characteristic component. Note that the position in the brain that generates the characteristic component of the electroencephalogram signal may be: the parietal, in the case of a P300 component of an event-related potential; the occiput, in the case of a P100 component of an Eye Fixation Related Potential, which concerns attention and concentration; the occiput also for alpha waves; or the temporal lobe for auditory stimulations.

In accordance with the above guidelines, a process of distinguishing a possibility of automatic restoration of a measurement electrode 23 and the method of restoration will be described.

At step S1411, based on the electrode information retained, the measurement electrode replacement section 16 calculates distances of the other non-insufficient electrodes from the position of the electrode which has become insufficient. However, the electrodes which are being used as the ground and the reference electrode cannot replace the measurement electrodes, and therefore are excluded from calculation. Also, the measurement electrode replacement section 16 retains the position of the generation source of the characteristic component, and calculates its distance from each electrode. In the example of FIG. 25, the distances of electrode numbers 1, 2, 5, 6, 8, and 9 from the coordinates (0,−2,0) are calculated.

At step S1412, the measurement electrode replacement section 16 compares the calculated distance information of the insufficient electrode against a threshold value in order to determine electrodes which are replacement candidates for the measurement electrode, i.e., electrodes which can similarly measure the characteristic component. The threshold value is set to a value beyond which the electroencephalographic characteristics will presumably change (e.g., 2 cm in the case of an adult). In the example of FIG. 25, electrodes 1 and 2, whose distance is 2 cm, are selected as replacement candidates.

If an electrode which is capable of similar measurement of the characteristic component of the electroencephalogram signal exists at step S1412, the measurement electrode replacement section 16 at step S1413 replaces the measurement electrode that has become insufficient with an electrode which is a replacement candidate for the measurement electrode, and restarts electroencephalogram measurement. The method of replacement can be realized by, for example, rerouting the circuit involving the electrode that has become insufficient to the replacement candidate electrode.

If there exist a plurality of electrodes which are capable of similar measurement of the characteristic component, an electrode whose distance from the generation source of the characteristic component is the closest is chosen as a replacing electrode for the measurement electrode, and the electrode replacement process is ended. In the present embodiment, the characteristic component is a P300 component, which is known to appear at the parietal. Considering the shape of the HMD, the parietal position is position (5,0,15), as shown in FIG. 24. Thus, a comparison between position (5,0,15) of the generation source of the characteristic component and the distances of electrodes 1 and 2 selected at step S1412 shows that electrode 1 has the smaller distance. Therefore, electrode 1 is chosen as the replacing electrode for the insufficiency measurement electrode. The electrode replacement is realized by stopping the electroencephalogram measurement utilizing the insufficient electrode, and beginning an electroencephalogram measurement utilizing the replacing electrode. For example, the electrode replacement is realized by rerouting the wiring for the insufficient electrode and its differential amplifier 40 (FIG. 1) to the wiring for the replacing electrode and its differential amplifier 40 (FIG. 1).

If step S1412 determines that no replacement candidate electrode exists, the measurement electrode replacement section 16 instructs the output section 13 to notify the user 10 that automatic restoration cannot be made, and the electrode replacement process is ended. As illustrated by the examples in FIGS. 17A to 17C, the output section 13 notifies the user 10 that an electrode insufficiency has occurred but automatic restoration cannot be made, through notification via alarm indication, an LED, etc., or notification via an audio or the like.

Next, an electrode replacement process for the reference electrode 22 will be described.

Since the reference electrode is an electrode to be utilized as the basis of electroencephalogram measurement, it needs to be a neutral electrode upon which electroencephalographic response is not measured. Therefore, if the reference electrode becomes insufficient, the reference electrode needs to be replaced by an electrode having characteristics such that it has little electroencephalographic response (electroencephalogram is not likely to be measured). Sites having little electroencephalographic response are the ear (mastoid) peripheries, which are at far distances from the brain, and therefore the reference electrode may be adopted from an ear periphery. Therefore, an electrode to replace a reference electrode which has become insufficient is similarly adopted from an ear periphery. In accordance with this, a process of distinguishing a possibility of automatic restoration of the reference electrode 22 and the method of restoration will be described.

At step S1421, based on the electrode information retained and the ear coordinates which are set in advance, the measurement electrode replacement section 16 calculates distances between an ear and the respective electrodes which are normally worn. However, the electrodes which are being used as the ground and the measurement electrodes cannot replace the electrode, and therefore are excluded from calculation. In the present embodiment, a mastoid position, which is the position of electrode number 10, has ear coordinates (−3,7,12). Therefore, the distances of electrodes 1, 2, 5, 6, 8, and 9 from (−3,7,12) are calculated.

At step S1422, the measurement electrode replacement section 16 compares the calculated distance information from the ear position against a threshold value in order to determine electrodes which are replacement candidates for the reference electrode, i.e., electrodes which are close to the ear position. Similarly to the measurement electrodes, the threshold value is set to e.g. 2 cm, beyond which the electroencephalographic characteristics will presumably change. In the example of FIG. 25, electrode 9, whose distance from the ear coordinates is 2 cm, is selected as a replacement candidate.

If electrodes close to the ear position exist at step S1422, the measurement electrode replacement section 16 at step S1413 replaces the reference electrode with an electrode whose distance from the ear position is the smallest, and restarts electroencephalogram measurement. The method of replacement can be realized by, for example, rerouting the circuit involving the electrode that has become insufficient to the replacement candidate electrode. Herein, electrode 9 is substituted by the reference electrode.

If step S1422 determines that no electrode exists that is close to the ear position, the measurement electrode replacement section 16 instructs the output section 13 to notify the user 10 that automatic restoration cannot be made, and the electrode replacement process is ended.

Finally, an electrode replacement process for the ground 21 will be described.

The ground is an electrode which is needed for achieving differential amplification, and is not place-dependent; the ground may simply be in contact with the skin of the user 10 to exhibit a sufficient function. Therefore, the ground should be replaced by an electrode having characteristics such that it has little possibility of being used as an electroencephalogram measurement electrode or reference electrode. In accordance with this, a process of distinguishing a possibility of automatic restoration of the ground 21 and the method of restoration will be described.

At step S1431, based on the electrode information and the position of the generation source of the characteristic component which is set in advance, the measurement electrode replacement section 16 calculates distances between the generation source of the characteristic component and the respective electrodes which are normally worn. In the present embodiment, the distances of electrodes 1, 2, 5, 6, 8, and 9 from the generation source (5,0,15) are calculated.

At step S1432, based on the electrode information, the measurement electrode replacement section 16 determines whether any replacement candidates for the ground exist or not, i.e., electrodes that are currently used neither as the reference electrode nor as the measurement electrodes. In the example of FIG. 25, electrodes 1, 2, 5, 6, 8, and 9 are selected as replacing electrodes.

At step S1432, if there exists any electrode that is used neither as the reference electrode nor as the measurement electrodes, the measurement electrode replacement section 16 at step S1433 replaces the ground with a ground replacement candidate electrode whose distance from the signal source as calculated at step S1431 is the farthest, and restarts electroencephalogram measurement. In the example of FIG. 25, electrode 6, whose distance from the generation source of the characteristic component (5,0,15) becomes the replacing electrode. The method of replacement can be realized by, for example, modifying the circuit of a replacing electrode which used to be an active electrode so that electrical connection with an amplifier within the electrode no longer exists, and rerouting it to the circuit of the ground electrode which has become insufficient.

If step S1432 determines that there exists no electrode that is used neither as the reference electrode nor as the measurement electrodes, the measurement electrode replacement section 16 instructs the output section 13 to notify the user 10 that automatic restoration cannot be made, and the electrode replacement process is ended.

By thus making a determination through the above processes as to whether there exists any electrode that has similar electroencephalographic characteristics, a possibility of automatic restoration is determined, and an electrode that may be a candidate for replacement is selected, whereby an electroencephalogram electrode replacement process is realized.

With the above construction, even if an electrode insufficiency occurs, an automatic determination is made as to whether electroencephalogram measurement can be continued or not, and if it is possible, the electrode state is automatically restored. As a result, an electroencephalogram can be stably measured even in a daily-life environment where insufficiencies concerning the state of electrode attachment may occur, whereby the user's trouble of having to frequently correct the state of electrode attachment can be reduced, thus reducing the burden of the user.

Embodiments 1 and 2 have illustrated an example of an electrode attachment state determination system such that the electroencephalogram interface function and the electrode attachment state determination function are provided within a single housing (HMD); however, this construction is exemplary. The electrode attachment state determination function may be separately accommodated in a single housing, thus embodying an electrode attachment state determination apparatus.

An electrode attachment state determination system according to the present invention is broadly applicable to an electroencephalogram measurement system which determines the state or intent of a user from a measured electroencephalogram signal, and feeds back a result of determination. Specifically, in the case where electroencephalogram measurements are taken in a daily-life environment by using electrodes, it will be useful to incorporate the electrode attachment state determination system according to the present invention into a wearable device such as an electroencephalograph or an HMD, in order to determine whether the state of attachment of the electrodes has become insufficient or not. The electrode attachment state determination system according to the present invention is useful for constructing such an electroencephalogram interface system for inferring the state or intent of a user, and may be implemented as a computer program for incorporation therein.

While the present invention has been described with respect to preferred embodiments thereof, it will be apparent to those skilled in the art that the disclosed invention may be modified in numerous ways and may assume many embodiments other than those specifically described above. Accordingly, it is intended by the appended claims to cover all modifications of the invention that fall within the true spirit and scope of the invention.

What is claimed is:

1. An electrode attachment state determination system comprising:
   an electroencephalogram measurement unit for measuring an electroencephalogram signal of a user by using at least one set of electrodes, the set including a ground electrode, a reference electrode, and a measurement electrode;
   a frequency analysis section for performing a frequency analysis of the electroencephalogram signal;
   an insufficient electrode determination section for extracting at least one parameter of a total frequency power across and all bands and at least one parameter of a noise amount from a result of the frequency analysis, and through a comparison of a value of the at least one noise parameter against a predetermined noise threshold value and through a comparison of a value of the at least one total frequency power parameter against a predetermined total frequency power threshold value, determining whether the ground electrode, the reference electrode, or the measurement electrode has an insufficient state of attachment; and
   an output section for, when an insufficient state of attachment is determined, presenting information indicating the insufficient state of attachment of the electrode to the user;

wherein the electroencephalogram measurement unit measures a first potential difference between the ground electrode and the reference electrode and a second potential difference between the ground electrode and the measurement electrode, and measures the electroencephalogram signal based on a difference between the second potential difference and the first potential difference;

the electrode attachment state determination system further comprising an electrode restoration determination unit for determining, based on a signal measured by using an insufficient electrode which is determined as having an insufficient state of attachment, whether the insufficiency in the state of attachment of the insufficient electrode has been eliminated or not, wherein, when the insufficient electrode is one of the reference electrode and the measurement electrode, the electrode restoration determination unit calculates an average value and variance of the signal as measured by using the insufficient electrode, and, if both of the average value and the variance are zero, the electrode restoration determination unit determines that the insufficiency in the state of attachment of the insufficient electrode has not been eliminated, or if not both of the average value and the variance are zero, the electrode restoration determination unit determines that the insufficiency in the state of attachment of the insufficient electrode has been eliminated.

2. The electrode attachment state determination system of claim 1, wherein the insufficient electrode determination unit extracts the noise amount parameter from the result of the frequency analysis, and if the noise amount parameter has a value exceeding a predetermined first threshold value as the noise threshold value, determines that the ground electrode has an insufficient state of attachment.

3. The electrode attachment state determination system of claim 2, wherein the insufficient electrode determination unit further extracts the total frequency power parameter from the result of the frequency analysis, and if the total frequency power parameter has a value exceeding a predetermined second threshold value as the total frequency power threshold value, determines that one of the reference electrode and the measurement electrode has an insufficient state of attachment.

4. The electrode attachment state determination system of claim 3, wherein, the electroencephalogram measurement section uses a plurality of sets of electrodes each including a ground electrode, a reference electrode, and a measurement electrode, to measure an electroencephalogram signal with each set;

the frequency analysis section performs a frequency analysis of each electroencephalogram signal; and the insufficient electrode determination unit extracts a noise amount parameter from a result of the frequency analysis of each electroencephalogram signal, and if all of the extracted noise amount parameters have values exceeding a predetermined first threshold value, determines that the ground electrode has an insufficient state of attachment, and extracts a total frequency power parameter from the result of the frequency analysis of each electroencephalogram signal, and if all of the extracted total frequency power parameters have values exceeding a predetermined second threshold value, determines that the reference electrode has an insufficient state of attachment, or if some of the extracted total frequency power parameters have values exceeding the second threshold value, determines that the measurement electrode has an insufficient state of attachment.

5. The electrode attachment state determination system of claim 1, wherein, a noise being steadily mixed from an external environment at a previously identified frequency is superposed on the electroencephalogram signal; and from the result of the frequency analysis, the insufficient electrode determination section extracts a frequency power of the noise as the noise amount parameter.

6. The electrode attachment state determination system of claim 5, wherein the previously identified frequency is a frequency of a commercial-power noise of a device which is in the external environment.

7. The electrode attachment state determination system of claim 1, wherein, as the total frequency power parameter, the insufficient electrode determination section extracts an average value of a power of the electroencephalogram signal in an analyzable frequency band.

8. The electrode attachment state determination system of claim 1, wherein, when the insufficient electrode is the ground electrode, the electrode restoration determination unit extracts the noise amount parameter from the result of the frequency analysis of the signal as measured by using the insufficient electrode, and, if the noise amount parameter has a value exceeding a predetermined first threshold value, the electrode restoration determination unit determines that the insufficiency in the state of attachment of the insufficient electrode has not been eliminated, or if the noise amount parameter does not have a value exceeding the predetermined first threshold value, the electrode restoration determination unit determines that the insufficiency in the state of attachment of the insufficient electrode has been eliminated.

9. An electrode attachment state determination system comprising:

an electroencephalogram measurement unit for measuring an electroencephalogram signal of a user by using at least one set of electrodes, the set including a ground electrode, a reference electrode, and a measurement electrode;

a frequency analysis unit for performing a frequency analysis of the electroencephalogram signal;

an insufficient electrode determination unit for extracting at least one parameter of a total frequency power across all bands and at least one parameter of a noise amount from a result of the frequency analysis, and through a comparison of a value of the at least one noise parameter against a predetermined noise threshold value and through a comparison of a value of the at least one total frequency power parameter against a predetermined total frequency power threshold value, determining whether the ground electrode, the reference electrode, or the measurement electrode has an insufficient state of attachment; and an output unit for, when an insufficient state of attachment is determined, presenting information indicating the insufficient state of attachment of the electrode to the user;

wherein the electroencephalogram measurement unit measures a first potential difference between the ground electrode and the reference electrode and a second potential difference between the ground electrode and the measurement electrode, and measures the electroencephalogram signal based on a difference between the second potential difference and the first potential difference;

the electrode attachment state determination system further comprising a measurement electrode replacement unit for, based on prestored electrode information, replacing an insufficient electrode which is determined as having an insufficient state of attachment with a replacing electrode, wherein, the electrode information describes information of a type and position of each of electrodes which are available for measuring an electroencephalogram signal of the user;

with respect to an insufficient electrode which is determined as having an insufficient state of attachment, the measurement electrode replacement unit identifies the type and position of the insufficient electrode, and refers to the electrode information to identify the replacing electrode based on electroencephalographic characteristics of an electroencephalogram signal to be measured by the insufficient electrode; and instead of the insufficient electrode, the electroencephalogram measurement unit uses the identified replacing electrode to measure an electroencephalogram signal.

10. The electrode attachment state determination system of claim 9, further comprising an electroencephalogram processing unit for distinguishing an intent of the user by utilizing a characteristic component contained in the measured electroencephalogram signal, wherein, when the insufficient electrode is the measurement electrode, the measurement electrode replacement section refers to the electrode information to identify, as the replacing electrode, an electrode which is within a predetermined distance from the insufficient electrode and which is at a closest distance from a brain position where the characteristic component of the electroencephalogram signal is generated.

11. The electrode attachment state determination system of claim 9, further comprising an electroencephalogram processing unit for distinguishing an intent of the user by utilizing a characteristic component contained in the measured electroencephalogram signal, wherein, when the insufficient electrode is the reference electrode, the measurement electrode replacement section refers to the electrode information to identify, as the replacing electrode, an electrode which is within a predetermined distance from a mastoid.

12. The electrode attachment state determination system of claim 1, further comprising an electroencephalogram processing unit for distinguishing an intent of the user by utilizing a characteristic component contained in the measured electroencephalogram signal, and executing a process which is in accordance with the intent of the user, wherein, from a result of the frequency analysis, the insufficient electrode determination section extracts at least one parameter of a total frequency power and a noise amount, and through a comparison of a value of the at least one parameter against a predetermined threshold value, determines a state of attachment of the ground electrode, the reference electrode, or the measurement electrode to be sufficient or insufficient; and if the state of attachment is determined to be insufficient, the output unit presents information indicating the insufficient state of attachment of the electrode to the user, and if the state of attachment is determined to be sufficient, the output unit outputs a result of the process which is in accordance with the intent of the user.

13. An electrode attachment state determination method comprising the steps of:

measuring an electroencephalogram signal of a user by using at least one set of electrodes including a ground electrode, a reference electrode, and a measurement electrode;

performing a frequency analysis of the electroencephalogram signal;

from a result of the frequency analysis, extracting at least one parameter of a total frequency power across all bands and at least one parameter of a noise amount, and through a comparison of a value of the at least one noise parameter against a predetermined noise threshold value and through a comparison of a value of the at least one total frequency power parameter against a predetermined total frequency power threshold value, determining whether the ground electrode, the reference electrode, or the measurement electrode has an insufficient state of attachment; and when an insufficient state of attachment is determined, outputting a notification to the user indicating a position and a type of electrode that has become insufficient wherein measuring an electroencephalogram signal of a user includes measuring a first potential difference between the ground electrode and the reference electrode and a second potential difference between the ground electrode and the measurement electrode, and measuring the electroencephalogram signal based on a difference between the second potential difference and the first potential difference;

determining, based on a signal measured by using an insufficient electrode which is determined as having an insufficient state of attachment, whether the insufficiency in the state of attachment of the insufficient electrode has been eliminated or not, wherein, when the insufficient electrode is one of the reference electrode and the measurement electrode, calculating an average value and variance of the signal as measured by using the insufficient electrode, and, if both of the average value and the variance are zero, determining that the insufficiency in the state of attachment of the insufficient electrode has not been eliminated, or if not both of the average value and the variance are zero, determining that the insufficiency in the state of attachment of the insufficient electrode has been eliminated.

14. A non-transitory computer-readable storage medium storing a computer program to be executed by a computer for determining a state of electrode attachment, wherein the computer program causes the computer to execute the steps of:

measuring an electroencephalogram signal of a user by using at least one set of electrodes including a ground electrode, a reference electrode, and a measurement electrode;

performing a frequency analysis of the electroencephalogram signal;

from a result of the frequency analysis, extracting at least one parameter of a total frequency power across all bands and at least one parameter of a noise amount, and through a comparison of a value of the at least one noise parameter against a predetermined noise threshold value and through a comparison of a value of the at least one total frequency power parameter against a predetermined total frequency power threshold value, determining whether the ground electrode, the reference electrode, or the measurement electrode has an insufficient state of attachment; and when an insufficient state of attachment is determined, outputting a notification to the user indicating a position and a type of electrode that has become insufficient;

wherein measuring an electroencephalogram signal of a user includes measuring a first potential difference between the ground electrode and the reference electrode and a second potential difference between the ground electrode and the measurement electrode, and measuring the electroencephalogram signal based on a difference between the second potential difference and the first potential difference;

determining, based on a signal measured by using an insufficient electrode which is determined as having an insufficient state of attachment, whether the insufficiency in the state of attachment of the insufficient electrode has been eliminated or not, wherein, when the insufficient electrode is one of the reference electrode and the measurement electrode, calculating an average value and variance of the signal as measured by using the insufficient electrode, and, if both of the average value and the variance are zero, determining that the insufficiency in the state of attachment of the insufficient electrode has not been eliminated, or if not both of the average value and the variance are zero, determining that the insufficiency in the state of attachment of the insufficient electrode has been eliminated.

* * * * *